US008353927B2

(12) United States Patent
Lampropoulos et al.

(10) Patent No.: US 8,353,927 B2
(45) Date of Patent: Jan. 15, 2013

(54) RADIAL ARTERY COMPRESSION DEVICE

(75) Inventors: Fred P. Lampropoulos, Salt Lake City, UT (US); Gregory R. McArthur, Sandy, UT (US)

(73) Assignee: Merit Medical Systems, Inc., South Jordan, UT (US)

( * ) Notice: Subject to any disclaimer, the term of this patent is extended or adjusted under 35 U.S.C. 154(b) by 926 days.

(21) Appl. No.: 12/435,227

(22) Filed: May 4, 2009

(65) Prior Publication Data

US 2010/0280541 A1  Nov. 4, 2010

(51) Int. Cl.
*A61B 17/00* (2006.01)
(52) U.S. Cl. ........ 606/204; 606/201; 606/203; 600/499; 24/486; 24/569; 251/8
(58) Field of Classification Search .................. 606/201, 606/203, 204; 600/499; 24/486, 569; 251/8
See application file for complete search history.

(56) References Cited

U.S. PATENT DOCUMENTS

| | | | |
|---|---|---|---|
| 1,281,653 A | 10/1918 | Plummer | |
| 2,332,107 A | 10/1943 | Nieburgs | |
| 3,050,064 A | 8/1962 | Moore et al. | |
| 3,376,846 A | 4/1968 | Sekiguchi et al. | |
| 4,307,799 A | 12/1981 | Zouzoulas | |
| 4,479,495 A | 10/1984 | Isaacson | |
| 4,557,262 A | 12/1985 | Snow | |
| 5,139,512 A | 8/1992 | Dreiling et al. | |
| 5,304,186 A | 4/1994 | Semler et al. | |
| 5,304,201 A | 4/1994 | Rice | |
| 5,728,120 A | 3/1998 | Shani et al. | |
| 6,068,646 A * | 5/2000 | Lam | ............................ 606/203 |
| 6,833,001 B1 | 12/2004 | Chao | |
| 7,780,612 B2 | 8/2010 | Ross | |
| 2003/0055453 A1 | 3/2003 | Akerfeldt | |
| 2005/0113866 A1* | 5/2005 | Heinz et al. | ................... 606/203 |

(Continued)

FOREIGN PATENT DOCUMENTS

CN  201205292  3/2009

(Continued)

OTHER PUBLICATIONS

Response to Office Action dated Sep. 27, 2011 for U.S. Appl. No. 12/349,405.
Office Action dated Dec. 8, 2011 for U.S. Appl. No. 12/349,405.
Notification of Transmittal of the International Search Report and the Written Opinion of the International Searching Authority issued Nov. 18, 2009 in International Application No. PCT/US2009/042868.

(Continued)

*Primary Examiner* — Gary Jackson
*Assistant Examiner* — Kevin Everage
(74) *Attorney, Agent, or Firm* — Stoel Rives LLP

(57) ABSTRACT

A radial artery compression device configured to be secured to a wrist or other portion of a patient to provide adjustable and consistent compression pressure in the area of a radial artery access site or other physiological portion of a patient to achieve hemostasis either during or after a medical procedure such as a percutaneous coronary procedure. The radial artery compression device includes a rotatable member and a compression pad adapted such that rotation of the rotatable member does not affect the rotational orientation of the compression pad. According to one embodiment of the present invention, a single rotation of the rotatable member results in complete extension or retraction of the radial artery compression device. According to another embodiment of the present invention, the rotation of the rotatable member results in a compounding of the extension or retraction of the compression pad relative to the body of the radial artery compression device.

22 Claims, 11 Drawing Sheets

U.S. PATENT DOCUMENTS

| | | | |
|---|---|---|---|
| 2005/0125025 A1 | 6/2005 | Rioux | |
| 2006/0058841 A1 | 3/2006 | Mills et al. | |
| 2007/0239092 A1* | 10/2007 | Ross | 602/20 |
| 2009/0281565 A1 | 11/2009 | McNeese | |

FOREIGN PATENT DOCUMENTS

| | | |
|---|---|---|
| DE | 4006696 A | 11/1990 |
| FR | 2828231 A | 2/2003 |

OTHER PUBLICATIONS

Medplus, Inc., "Tourniquet (Radial Artery Compression Device)", http://www.bikudo.com/product_search/details/187473/tourniquet_radial_artery_compression_device.html, Nov. 24, 2009.

Office Action dated Mar. 2, 2011 for U.S. Appl. No. 12/349,405.

Office Action dated Jun. 28, 2011 for U.S. Appl. No. 12/349,405.

* cited by examiner

RADIAL ARTERY COMPRESSION DEVICE

BACKGROUND OF THE INVENTION

1. Field of the Invention

The present disclosure relates to a radial artery compression device. In more particular, the present disclosure relates to a radial artery compression device configured to provide an adjustable level of compression pressure on the radial artery to achieve hemostasis at, or in the area of, a vascular access site.

2. Relevant Technology

Medical advancements have resulted in the ability to diagnose and treat coronary artery disease using vascular delivery apparatus and techniques. One advantage of coronary procedures utilizing vascular delivery is that a practitioner can access a desired position within the patient's body without administering general anesthetic or requiring highly invasive surgery. During a typical procedure, a sheath having a haemostatic valve is utilized to access a peripheral artery utilizing the administration of a local anesthetic at the vascular access site. A pre-shaped catheter is then introduced into the patient's vasculature through the sheath. The catheter can then be advanced to the ostium of the relevant coronary artery or to another desired location within the patient. The catheter enables delivery of medical instruments, medicines or fluids such as radiography contrast medium, angioplasty wires, balloons, and stents. During or after completion of the procedure, the sheath and catheter are removed and hemostasis can be achieved by manual compression, suturing the access site, or by utilizing another direct repair procedure.

Often these percutaneous coronary diagnostic and interventional procedures are accomplished through the radial artery of a patient. Radial artery access has the potential advantages of reduced access site complications, rapid patient mobilization, and reduced costs. The relatively superficial position of the distal radial artery enables direct application of compression to the artery to achieve and maintain hemostasis during a procedure. Additionally the radial artery allows quick and direct closure at the catheter access site as soon as the arterial catheter has been removed at the end of the procedure.

As with any arterial puncture, achieving hemostasis during and/or after a procedure can be challenging. Typically the access site, or opening, in the artery is created utilizing a micropuncture apparatus, dilator or can even be formed utilizing a single straight incision to form a slit in the artery. The pulsatile nature of arterial blood flow may present challenges to achieving hemostasis at the access site. As a result of this and other factors, during the course of the procedure, blood may leak through the access site and around the outside diameter of the sheath or catheter. Existing devices are not adapted to provide desired and/or adjustable compression to the radial artery at the vascular access site during the course of a procedure.

When the procedure has been completed, typically the catheter is removed and the practitioner or medical professional will apply pressure at the vascular access site to achieve hemostasis and effectuate closure of the vascular access site. One technique for achieving hemostasis is to apply pressure at, or at a point slightly upstream, of the vascular access site. Typically, continuous pressure is necessary to stop bleeding and achieve hemostasis at the access site. While the applied pressure should remain relatively constant, there are advantages to applying a higher level of compression pressure at the beginning of the compression period and then reducing the level of compression pressure after a determined amount of time has elapsed. By gradually reducing the compression pressurization during the compression period, while continually maintaining at least a threshold level of compression, blood can begin to flow through the artery at a reduced pressure, providing nutrient rich blood to the tissue downstream from the access site. Blood flowing through the artery can then hasten clotting to enable hemostasis without application of ongoing compression. Not only can this provide improved closure, but also can improve the relative comfort of the patient.

Compression is typically applied to an access site by a nurse or other practitioner by manually holding a dressing at the access site. Although employing a practitioner to provide compression permits the gradual reduction of pressurization at the access site, it can also be a costly use of practitioner time. Alternative existing radial artery compression techniques which do not require the ongoing manual application of pressure by the practitioner may employ tape or a compression bandage at the vascular access site. These devices and techniques, while allowing the practitioner to attend to other matters, can render it difficult or impractical to adjust the compression pressure while maintaining continuous pressure. As a result, the tape or compression bandages may end up being positioned around the access site without being loosened or adjusted until they are removed. Additionally, the compression provided by such techniques can be poorly applied, insufficient to provide proper pressurization and/or may be poorly tailored for the exigencies of the particular procedure.

BRIEF SUMMARY OF THE INVENTION

Figure 1:
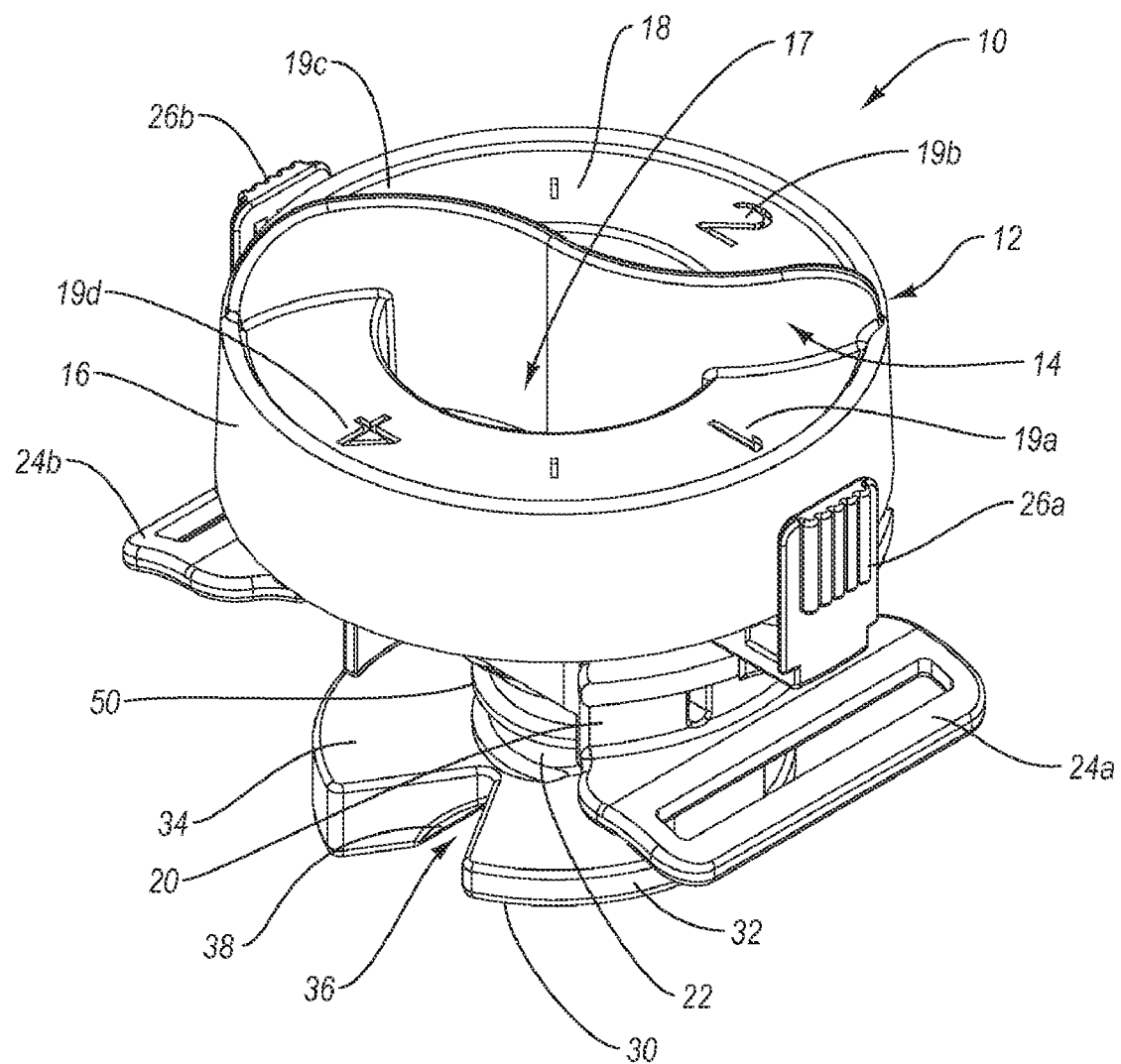
FIG. 1 is a perspective view of an improved radial artery compression device according to one aspect of the present invention.

The present invention is directed to an improved radial artery compression device. The radial artery compression device is adapted to allow a user to provide varying degrees of pressurization against a patient's radial artery in order to maintain a desired degree of hemostasis at a percutaneous catheter access site. The radial artery compression device includes a rotatable member and a compression pad. The rotatable member allows a practitioner to actuate the compression pad to provide an increased or decreased amount of pressurization against a patient's radial artery.

According to one aspect of the present invention, the radial artery compression device can be secured to a patient's wrist utilizing a strap, wrist band or other mechanism. Upon actuation of the rotatable member, the compression pad can be extended away from a body of the radial artery compression device. When the compression pad is extended away from the body of the radial artery compression device an increased amount of pressurization is provided against the radial artery. In the event that a catheter is positioned within the radial artery, the configuration of the surface of the compression pad secures the wall of the radial artery against the outside diameter of the catheter positioned therein. In this manner, the radial artery compression device can maintain hemostasis of the radial artery relative to the catheter. In other words, a practitioner can actuate the radial artery compression device to secure a catheter within a patient's radial artery while providing a desired degree of hemostasis at the percutaneous access site. As a result, the radial artery compression device allows the practitioner to turn his/her attention to other aspects of the procedure being done.

Once the practitioner has substantially completed a procedure and is ready to remove the catheter from the patient's radial artery, the practitioner can easily retract the compression pad relative to the body of the radial artery compression device. Retraction of the compression pad relative to the body of the radial artery compression device removes the compression pressurization which helps to maintain the catheter within the patient's radial artery. As a result, the practitioner can remove the catheter from within the patient's radial artery.

The configuration of the radial artery compression device allows the practitioner to actuate the rotatable member utilizing a single hand, thus freeing the other hand of the practitioner to perform other aspects of a procedure. For example, the practitioner can hold a catheter within a percutaneous access site in the patient's wrist while actuating the rotatable member to extend the compression pad and secure the catheter within the patient's radial artery. Alternatively, the practitioner can slowly deactuate the rotatable member of the radial artery compression device in order to withdraw the compression pad relative to the body of the radial artery compression device and remove the catheter from the patient's wrist.

According to one aspect of the present invention, the radial artery compression device includes a threaded shaft which is secured to the rotatable member. The threaded shaft threadably engages the body of the radial artery compression device such that actuation of the threaded shaft results in a first amount of movement of the threaded shaft. A secondary shaft is provided in threaded communication with the threaded shaft which is secured to the rotatable member. In this manner, a compound threading action is provided upon rotation of the rotatable member. In other words, when the rotatable member is rotated by the user, a first amount of axial displacement is provided by the threaded shaft. A second amount of axial displacement is provided in addition to the first amount of axial displacement by the secondary threaded shaft. In this manner, a desired degree of rotation of the rotatable member provides an increased amount of axial displacement of the compression pad relative to the body of the radial artery compression device.

According to another aspect of the present invention, a body of the radial artery compression device provides a structure upon which the other components of the radial artery compression device are secured. A rotatable member is provided on the upward facing portion of the body and the compression pad is located on the downward facing portion of the body of the radial artery compression device. The rotatable member includes a threaded shaft which is threaded through the body of the radial artery compression device. The body of the radial artery compression device includes a threaded aperture which threadably engages the threaded shaft of the rotatable member. In this manner, rotation of the rotatable member and the cooperative engagement of the thread shaft of the rotatable member and the threaded aperture of the body results in axial displacement of both the rotatable member and the threaded shaft. A secondary threaded shaft is provided in connection with the compression pad. As a result, when a user rotates the rotatable member, the threaded interaction between the threaded shaft of the rotatable member and the threaded shaft of the compression pad results in axial displacement of both the compression pad and the secondary threaded shaft relative to the rotatable member. As a result, a compounding effect is effectuated in which rotation of the rotatable member provides a greater amount of axial displacement than would be provided by cooperative engagement of the primary threaded shaft with the threaded aperture of the body of the radial artery compression device.

According to one aspect of the present invention, a threaded shaft is formed of rigid material and is disposed through the body of the radial artery compression device. The threaded shaft is positioned between the rotatable member and the compression pad of the radial artery compression device. The threaded shaft threadably engages the body allowing movement of the rotatable member relative to the body. A second shaft formed of rigid material is also provided. The second shaft is positioned between the rotatable member and the compression pad. The second shaft threadably engages the first shaft such that the threaded engagement between the first shaft and the second shaft results in movement of the compression pad with respect to the body as the rotatable member is rotated relative to the body. As a result, rotation of the rotatable member in a first direction is configured to increase the amount of compression applied to the radial artery by the compression pad. The rotation of the rotatable member in a second direction is adapted to decrease the amount of compression applied to the radial artery by the compression pad.

According to one aspect of the present invention, the configuration of the rotatable member and compression pad is such that inadvertent rotational movement of the compression pad is prevented. For example, in one embodiment the first threaded shaft and the second threaded shaft engage one another such that the axial movement of the compression pad relative to the body of the radial artery compression device does not result in rotational movement of the compression pad. In another embodiment, body engagement posts are secured relative to the compression pad to minimize or prevent rotational movement of the compression pad relative to the body of the radial artery compression device.

Minimizing rotational movement of the compression pad can be desirable for a variety of reasons. For example, the compression pad can include a notch or step which is desired to be aligned with the radial artery or catheter. The compression pad can provide a desired curvature which conforms to the outside diameter of the catheter and/or the structure of the radial artery. By controlling rotational movement of the compression pad, the desired alignment of the features of the compression pad can be maintained without additional user attention or manipulation. Additionally, the first and second sides of the contact surface of the compression pad can be adapted to conform to the physiological features of a patient's wrist to provide a desired amount of contact between the compression pad and the patient's wrist when the desired rotational alignment of the compression pad is maintained. As a result, maintaining the rotational alignment of the compression pad of the radial artery compression device throughout the course of the procedure, despite rotation of the rotatable member during the procedure, can be important to maintain desired operability of the radial artery compression device.

According to another aspect of the present invention, the radial artery compression device includes ratchet engagement members. The ratchet engagement members permit rotation of the rotatable member in a first direction without additional manipulation by the user. However, the ratchet engagement members prevent rotation of the rotatable member in a second direction without first releasing the ratchet engagement members relative to the rotatable member. For example, in one embodiment, the user is allowed to rotate the rotatable member in a clockwise direction to extend the compression pad and thus apply an increased degree of compression on the radial artery. However, the user is not allowed to rotate the rotatable member in a counter-clockwise direction to retract the compression pad and result in a lesser amount of compression being applied to the radial artery. As a result, inadvertent or undesired releasing of the pressurization provided by the compression pad relative to the patient's wrist, radial artery, or catheter is controlled, thus ensuring desired compression on the patient's wrist during the course of the procedure. When the user desires to lessen the amount of pressurization on the patient's radial artery or to remove a catheter from the patient's artery, the user first disengages the ratchet mechanism to allow rotation of the rotatable member in the second rotational direction.

According to one embodiment of the present invention, the ratchet mechanism is positioned on an interior diameter of the rotatable member. According to another embodiment of the present invention, the ratchet engagement or disengagement members are buttons positioned on one or both sides of the rotatable member which are depressed by the user to release the engagement of the ratchet. According to yet another embodiment, the ratchet engagement member includes one or more ramps which permit rotation of the rotatable member in a first position while preventing or minimizing rotation of the rotatable member in a second direction.

DETAILED DESCRIPTION

FIG. 1 is a perspective view of a radial artery compression device 10 according to one embodiment of the present invention. Radial artery compression device 10 is adapted to allow a user to provide varying degrees of pressurization against a patient's radial artery or other position in a patient's vasculature to maintain a desired degree of hemostasis at a percutaneous access site. In the illustrated embodiment, radial artery compression device 10 comprises a rotatable member 12, a body 20, wrist straps securement members 24a, b, a compression pad 30, and a threaded shaft 50.

Body 20 is adapted to provide a framework upon which the other components of the radial artery compression device 10 can be positioned. In the illustrated embodiment rotatable member 12 and compression pad 30 are positioned on alternative sides of body 20. Compression pad 30 is positioned on the underside of body 20 such as to be positioned adjacent a patient's skin or other desired target of a pressurization procedure. Rotatable member 12 is positioned on the upper side of body 20. The positioning of rotatable member 12 relative to body 20 allows a practitioner to rotate rotatable member 12 in a desired manner so as to allow for proper actuation of radial artery compression device 10.

In the illustrated embodiment, rotatable member 12 is adapted to allow a practitioner to actuate or deactuate radial artery compression device 10. Additionally, rotatable member 12 allows a practitioner to incrementally increase or decrease the amount of pressurization provided by compression pad 30 throughout the course of a procedure. Rotatable member 12 comprises a handle member 14, a sidewall 16, a central void 17, an upper face 18, and indicia 19a-d. In the illustrated embodiment, a handle member 14 is provided to allow a user to grasp rotatable member 12 and to rotate rotatable member 12 in a desired manner. Handle member 14 has an arcuate S-curve type shape which provides an ergonomic and desired grip. The shape of handle member 14 allows a user to place a thumb and index finger on alternative sides of handle member 14 to twist rotatable member 12 in either a clockwise or counter-clockwise rotational direction. In this manner, an ergonomic and easy to grasp configuration is provided by handle member 14.

Central void 17 forms a circular recessed region in the center of rotatable member 12. Central void 17 is intersected by the arcuate configuration of handle member 14. In other words, handle member 14 extends from one lateral side of central void 17 to the opposing lateral side of central void 17. In this manner, a recess is provided relative to upper face 18 of rotatable member 12. Handle member 14 can extend from an elevation which extends above upper face 18 to a position within central void 17 which extends below upper face 18. The resultant hemispherical type voids on either lateral side of handle member 14 created by the juxtaposition of central void 17 and handle member 14 can receive the finger or thumb to grasp handle member 14 and cause rotation of rotatable member 12.

Upper face 18 in sidewall 16 forms the outer periphery of rotatable member 12. Sidewall 16 extends a determined amount in an upward direction such that a user can grasp the outer facing surface of sidewall 16 and rotate rotatable member 12. Additionally, sidewall 16 provides a thickness or overall elevational dimension to the body of rotatable member 12. Upper face 18 is positioned so as to face away from the body 20 of radial artery compression device 10. Upper face 18 includes a plurality of indicia 19a-d which provide the user an indicator of the rotational position of rotatable member 12. This allows a user to ascertain and perceive not only the current rotational position of rotatable member 12 but to ascertain the current rotational position relative to other rotational positions of rotatable member 12.

In the illustrated embodiment, the configuration of rotatable member 12 is such that a single rotation of rotatable member 12 causes extension of compression pad 30 through a range of at least half of the total possible axial movement of compression pad 30. As a result, when the user rotates rotatable member 12, a single rotation of rotatable member 12 will cause a substantial amount of movement of compression paid 30. Similarly, a single full rotation of rotatable member 12 results in a substantial pressurization increase by compression pad 30 on the radial artery or other physiological feature of a patient. As a result, when a first indicia is moved from one rotational position to a second rotational position, a user can ascertain the approximate amount of extension of compression pad 30 relative to body 20.

In the illustrated embodiment indicia 19a is a numeric indicia "1", indicia 19b is a numeric indicia "2", indicia 19c is a numeric indicia "3" (see FIG. 2B), and indicia 19d is a numeric indicia "4". In the illustrated embodiment indicia 19a is adjacent to a ratchet engagement member 26a and indicia 19d is adjacent to a ratchet engagement member 26b. When rotatable member 12 is rotated such that indicia 19a is positioned adjacent to ratchet engagement member 26b instead of being positioned adjacent to ratchet engagement member 26a, a practitioner can perceive that compression pad 30 has been extended a predetermined amount and a desired amount of pressurization is provided against a patient's wrist or other physiological feature. According to one embodiment of the present invention, a single rotation of rotatable member 12 results in a complete and full extension of compression pad 30 relative to body 20. In other words, a single rotation of rotatable member 12 moves compression pad 30 from a position in which compression pad 30 is fully retracted to a position of in which compression pad 30 is fully extended.

Wrist strap securement members 24a, b are integrally coupled to body 20 of radial artery compression device 10. Wrist strap securement members 24a, b are positioned on opposing lateral sides of body 20. Wrist strap securement members 24a, b include a loop or central bore which permits the threading of a strap, or other securement member which can be placed around a patient's wrist to secure radial artery compression device 10 relative to the wrist or other physiological feature of a patient.

Ratchet engagement members 26a, b are also positioned on opposing sides of body 20. Ratchet engagement members 26a, b project from the underside of rotatable member 12 and extend in an upward direction adjacent the sidewall 16 of rotatable member 12. Ratchet engagement members 26a, b are adapted to be grasped by the user and pushed inward in the direction of one another. Actuation of ratchet engagement members 26a, b disengages a ratchet mechanism associated with rotatable member 12 allowing rotation of rotatable member 12 in both a first direction and a second direction. In one embodiment, a user releases rotatable member 12 by biasing ratchet engagement member 26a toward ratchet engagement member 26b and by biasing ratchet engagement member 26b in the direction of ratchet engagement member 26a. Biasing ratchet engagement members 26a, b in the direction of one another effectively reduces the spatial distance between ratchet engagement member 26a and ratchet engagement member 26b. In this manner, an internal ratchet component which engages a component of rotatable member 12 is released allowing movement of rotatable member 12 in one or both of a clockwise and counter-clockwise direction.

According to one aspect of the present invention, the practitioner is allowed to rotate rotatable member 12 in a first rotational direction to extend compression pad 30 without actuating ratchet engagement members 26a, b. The ratchet mechanism associated with radial artery compression device 10 prevents rotation of rotatable member 12 in a second direction effectively securing compression pad 30 in a desired extended position. In this manner, during the course of a procedure a desired amount of compression can be consistently provided by radial artery compression device 10 without requiring the ongoing attention of the practitioner. Additionally, the practitioner can simply and quickly change the amount of compression provided by the radial artery compression device 10 by simple actuation of rotatable member 12.

In the event the practitioner desires to retract compression pad 30 relative to body 20 or otherwise lessen the amount of compression provided by radial artery compression device 10 relative to the patient, the user simply compresses ratchet engagement members 26a, b relative to one another. When ratchet engagement members 26a, b are compressed, the engagement of rotatable member 12 is released and rotation of rotatable member 12 in a reverse direction is permitted. Rotation of rotatable member 12 in a reverse direction allows retraction of compression pad 30 relative to body 20.

In the illustrated embodiment, a threaded shaft 50 is depicted. Threaded shaft 50 is actuated by rotation of rotatable member 12. When a user rotates rotatable member 12, threaded shaft 50 engages threaded members or other components of radial artery compression device 10 causing axial movement of compression pad 30 relative to body 20. For example, when rotatable member 12 is rotated in a first direction, the threaded shaft can engage a threaded member of body 20 resulting in extension of compression pad 30 relative to body 20. In other words, when rotatable member 12 is rotated in a first direction, compression pad 30 moves away from body 20. When rotatable member 12 is rotated in a second direction, the cooperative engagement of threaded shaft 50 with the threaded component of body 20 results in retraction of compression pad 30 relative to body 20. In other words, the distance between compression pad 30 and body 20 is decreased when rotatable member 12 is rotated in a second direction.

Compression pad 30 includes a first portion 32, a second portion 34, a notch 36, and a step 38. First portion 32 is positioned on one lateral side of step 38. Second portion 34 is position on the opposing side of compression pad 30. Notch 36 provides a cutout in the otherwise circular radius of compression pad 30. Notch 36 provides a pie shaped or angular cutout which is wider at the radius of compression pad 30 and gradually narrows to a point as the notch approaches the middle of compression pad 30. The configuration of notch 36 is such that the point of notch 36 is aligned with step 38. Step 38 runs from one lateral side of compression pad 30 to the opposing lateral side of compression pad 30.

In the illustrated embodiment, compression pad 30 includes a first portion 32 and a second portion 34. First portion 32 has a different elevation than second portion 34. For example, in the illustrated embodiment first portion 32 has a higher elevation such that the sidewall of compression pad 30 associated with first portion 32 has a minimal height. In contrast, second portion 34 has a lower elevation such that the sidewall of compression pad 30 associated with second portion 34 has a greater height than the sidewall of compression pad associated with first portion 32. Additionally, the distance between the contact surface of second portion 34 is further away from the upper surface of compression pad 30 than that of first portion 32.

The different elevational positions of first portion 32 and second portion 34 is adapted to conform to the physiological features on the underside of a patient's wrist. For example, the outside of a patient's wrist is somewhat depressed from the more central portion of a patient's wrist. As a result, the different elevational surfaces of compression pad 30 provided by first portion 32 and section portion 34 provide a better overall contact with the portions of the patient's wrist on either side of the patient's radial artery.

Step 38 provides a transition from first portion 32 to second portion 34. According to one embodiment of the present invention, step 38 has a curvilinear, arcuate, or radial dimension which can more closely approximate the outside diameter of a catheter which may be positioned within a patient's radial artery. Notch 36 provides desired compression around a percutaneous catheter access point such that the catheter is maintained in desired hemostasis within the patient's radial artery.

Figure 2A:
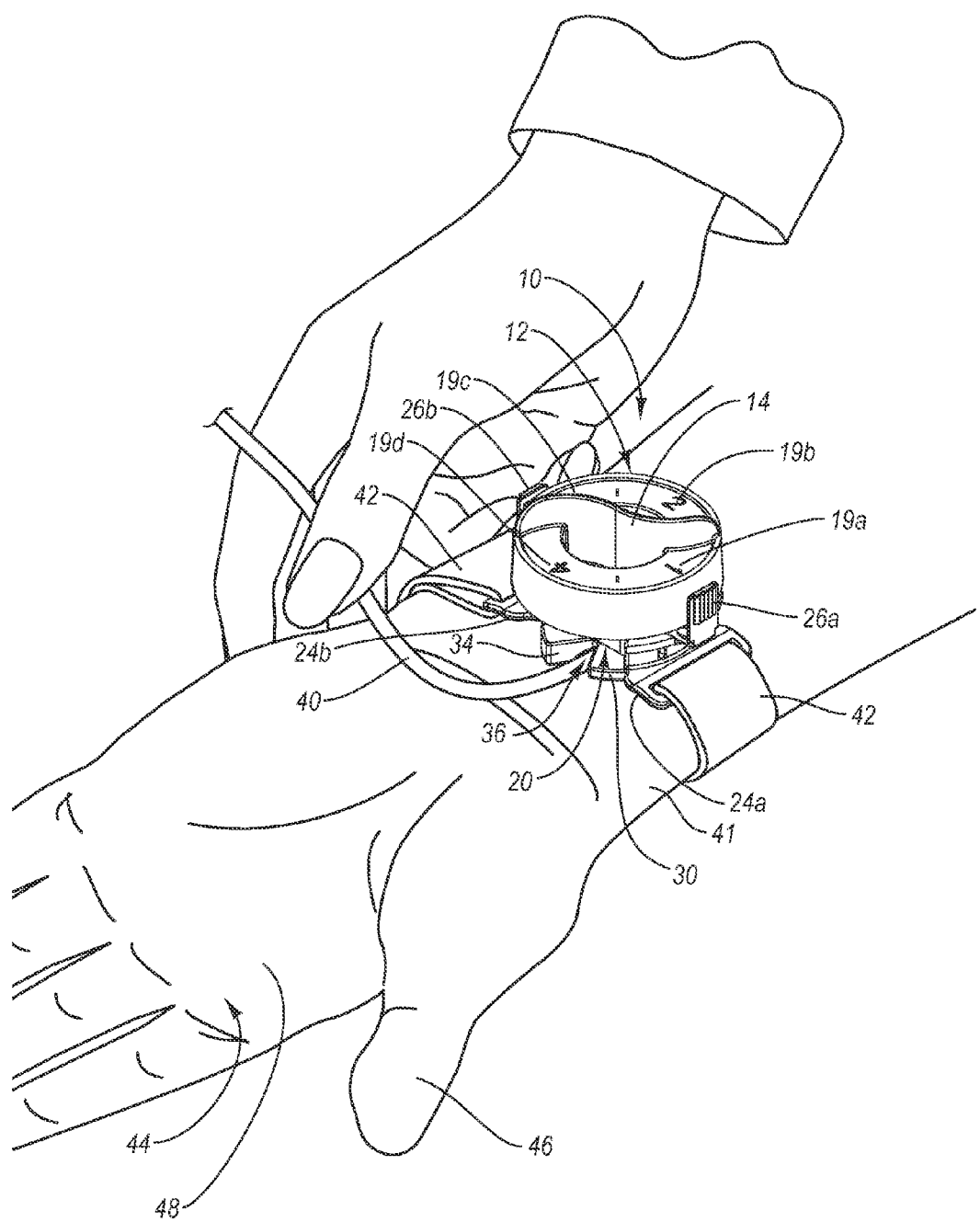
FIG. 2A is a perspective view a radial artery compression device of FIG. 1 illustrating use of the device on a patient.

FIG. 2A is a perspective of radial artery compression device 10 of FIG. 1 according to one embodiment of the present invention. In the illustrated embodiment, radial artery compression device 10 has been secured to a patient's wrist 41. A wrist strap 42 circumscribes a patient's wrist 41 and is secured to wrist strap securement members 24a, b. Additionally, radial artery compression device 10 is secured to the underside of patient's wrist 42. Radial artery compression device 10 is positioned such that compression pad 30 is adapted to be in contact with a lateral side of patient's wrist 41. Radial artery compression device 10 is positioned on the lateral side of patient's wrist 41 adjacent patient's thumb 46. This is due to the fact that the radial artery is positioned laterally within the patient's wrist on the same lateral side of the patient's wrist 41 as the patient's thumb 46.

In the illustrated embodiment, compression pad 30 is positioned such that it is in a retracted position relative to body 20. As a result, a minimal amount of compression is provided on the patient's wrist. A catheter 40 is positioned within the patient's radial artery. Compression pad 30 is positioned over catheter 40 such that notch 36 accommodates the portion of catheter 40 extending from patient's wrist 41. The juxtaposition of compression 30 relative to catheter 40 provides a desired amount of compression at the radial artery access site in which catheter 40 is entering the patient's radial artery. As will be appreciated by those skilled in the art, catheter 40 will typically be threaded from the thumb side of the patient's wrist and extend upward into the patient's arm. Additionally, notch 36 will be positioned on the hand side of the radial artery compression device 10. In the illustrated embodiment, a practitioner is holding catheter 40 to maintain the position of catheter 40 within the patient's radial artery prior to full actuation of radial artery compression device 10. In other words, in the illustrated embodiment radial artery compression device 10 has been secured to the patient's wrist, however rotatable member 12 has not yet been fully actuated. While radial artery compression device 10 has been secured to the patient's wrist, compression pad 30 has not been extended to a position to secure catheter 40 within the patient's radial artery. Once the radial artery compression device 10 has been secured to the patient's wrist 41 utilizing wrist strap 42, the practitioner can actuate rotatable member 12. Actuation of rotatable member 12 allows the practitioner to effectuate desired axial movement of compression pad 30 so as to cause desired compression of catheter 40 within the patient's radial artery.

The configuration of radial artery compression device 10 allows a practitioner to actuate rotatable member 12 utilizing a single hand. As a result, the practitioner can hold catheter 40 in one hand to maintain the desired position of the catheter 40 within the patient's radial artery while simultaneously actuating rotatable member 12 with the practitioner's other hand. As a result, radial artery compression device 10 allows for a single handed actuation and securement of a catheter within a patient's vasculature while permitting desired and often advantageous use of the practitioner's other hand in other aspects of the procedure.

Figure 2B:
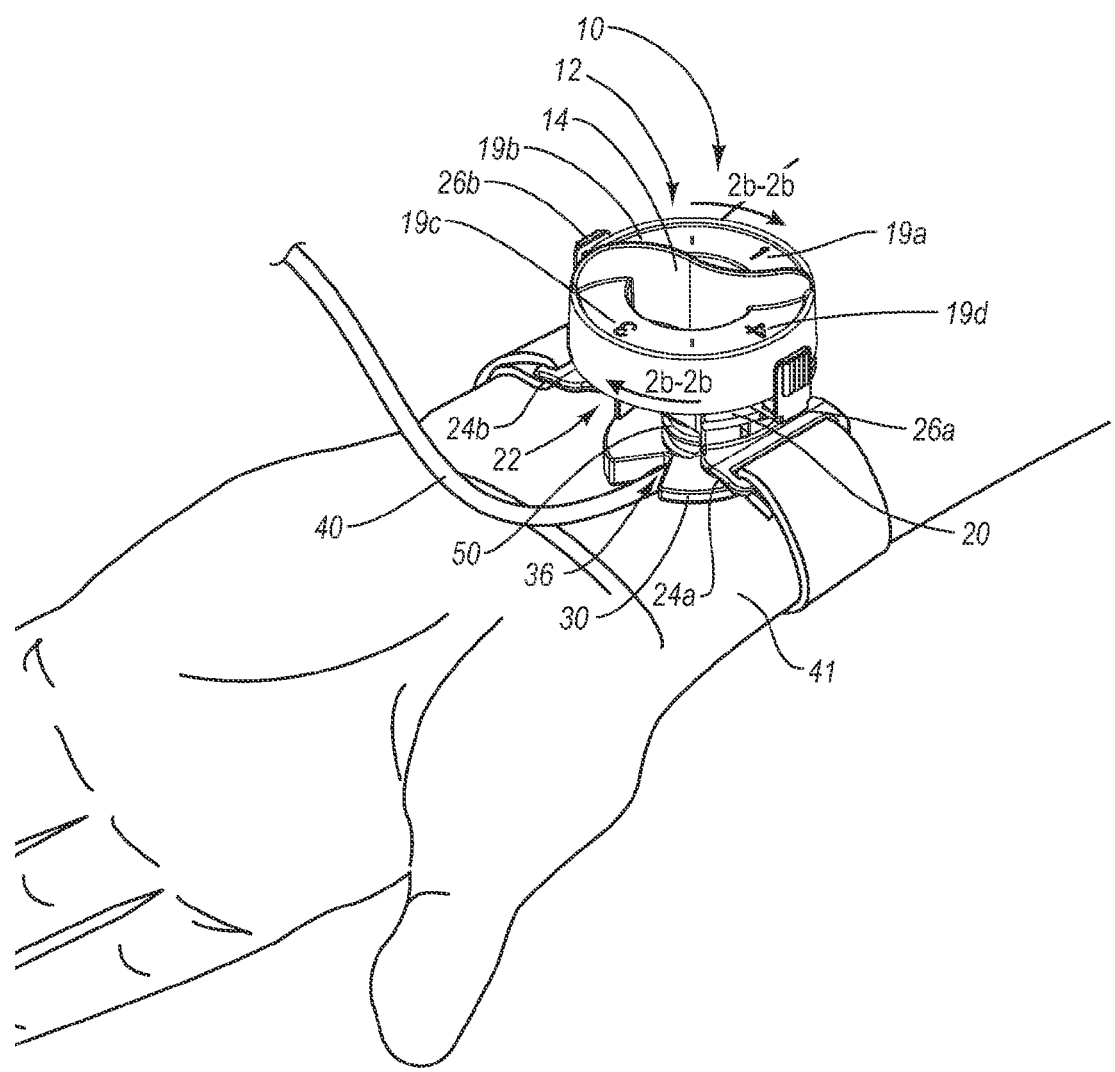
FIG. 2B is a perspective view of a radial artery compression device illustrating the manner in which the radial artery compression device can secure a catheter within a patient's radial artery according to one aspect of the present invention.

FIG. 2B is a perspective view of the radial artery compression device 10 of FIG. 2A. In the illustrated embodiment, rotational arrows 2b-2b are illustrated. Rotational arrows 2b-2b are indicative of a clockwise rotational direction of rotatable member 12. Rotation of rotatable member 12 in the clockwise rotational position as indicated by rotational arrow 2b-2b causes extension of compression pad 30 from within recess 22 of body 20. Recess 22 is adapted to accommodate compression pad 30 when compression pad 30 is in a fully retracted position.

Catheter 40 is positioned within a percutaneous access site allowing the threading of catheter 40 into the patient's radial artery. As previously discussed, catheter 40 will typically be threaded into the patient's artery from the hand side of the wrist and extend in the direction of the elbow of the patient. Once a practitioner has threaded catheter 40 to a desired position within the patient's radial artery, the practitioner can grasp a handle member 14 or other portion of rotatable member 12 and rotate rotatable member 12 in a clockwise rotational direction. As the practitioner rotates rotatable member 12 in a clockwise rotational direction, threads of threaded shaft 50 cooperatively engage other components of radial artery compression device 10 resulting in axial movement of compression pad 30. As the practitioner continues to rotate rotatable member 12, compression pad 30 moves from within recess 22 of body 20 such that the distance between compression pad 30 and body 20 begins to increase. As a result, compression pad 30 begins to exert increasing pressure on the patient's wrist 41. The portion of catheter 40 positioned within the patient's wrist is contacted by step 38 (see FIG. 1) on the on the underside of compression pad 30. In particular, due to the threading of catheter 40 beneath compression pad 30, pressure begins to be exerted on both the radial artery and in particular on the portion of the radial artery in which catheter 40 is positioned. In this manner, when a desired degree of compression is provided by compression pad 30, the configuration of compression pad 30 effectively seals catheter 40 within the radial artery of the patient. Additionally, the flow of blood from the percutaneous access site is stopped. As a result, radial artery compression device 10 provides a consistent and desired degree of compression on the percutaneous access site in the patient's wrist without requiring ongoing attention or manual compression by the practitioner. In other words, once the practitioner has fully actuated rotatable member 12, compression pad 30 will hold catheter 40 in place within the patient's vasculature while also minimizing or preventing bleeding at the catheter access site. This allows the practitioner to turn her/his attention to other aspects of the procedure to be performed.

In the illustrated embodiment, ratchet engagement members 26a, b, have not been depressed. As a result, rotational movement in a counter-clockwise direction, or a direction opposite to the rotational arrows 2b-2b is prevented. As a result, inadvertent releasing of the pressure provided by compression pad 30 is prevented. In the illustrated embodiment, the cooperative interaction between threaded shaft 50, body 20, and rotatable member 12 results in little or no rotational movement of compression pad 30 pursuant to rotation of rotatable member 12. In other words, as the user rotates rotatable member 12, the rotational position of notch 36 remains unchanged. As a result, a user can align notch 36 with catheter 40 and step 38 (see FIG. 1) along the patient's radial artery. Once the components of compression pad 30 are properly aligned, the practitioner can actuate rotatable member 12 without the risk that compression pad 30, and in particular notch 36 and step 38 (see FIG. 1), will remain in their correct rotational orientation relative to catheter 40 as the practitioner rotates rotatable member 12. For example, a user may position a notch of compression pad 30 over catheter 40. Additionally, step 38 (see FIG. 1) of compression pad 30 may be aligned over the portion of the radial artery in which catheter 40 extends. As the user rotates rotatable member 12, the positioning of notch 36 relative to the other components of radial artery compression device 10 remain unchanged.

In the illustrated embodiment, notch 36 is positioned at a rotational position which is approximately half way between ratchet engagement members 26a, b. Additionally, notch 36 is positioned approximately half way between wrist strap securement members 24a, b. As the user begins to rotate rotatable member 12, the rotational position of notch 36 remains unchanged relative to the components of body 20. As a result, during rotation of rotatable member 12, notch 36 remains positioned approximately half way between ratchet members 26a, b and wrist strap securement members 24a, b. This facilitates desired alignment and operation of the components of radial artery compression device 10 throughout the course of the compression procedure.

As will be appreciated by those skilled in the art, a variety of types and components of radial artery compression devices can be provided without departing from the scope and spirit of the present invention. For example, according to one embodiment of the present invention, a rotatable member which rotates in a counter-clockwise direction to actuate the compression pad is utilized. According to another embodiment of the present invention, a handle component, knob, or other actuation member having a configuration which is different than the rotatable member is utilized. According to another embodiment of the present invention, the compression pad is actuated utilizing a motion other than rotation. According to another embodiment of the present invention, actuation or reverse actuation of the rotatable member requires disengagement of a ratchet engagement member or other rotational securement component. In yet another embodiment, a compression pad has a contact surface or configuration that is different from that depicted in FIGS. 1-2B. For example, according to one embodiment of the present invention, the compression pad may have a soft or pliable component. In another embodiment, the compression pad may not include a notch portion. In yet another embodiment, the contact surface of the compression pad may have a somewhat flat or curved configuration rather than having first and second elevational components.

Figure 2C:
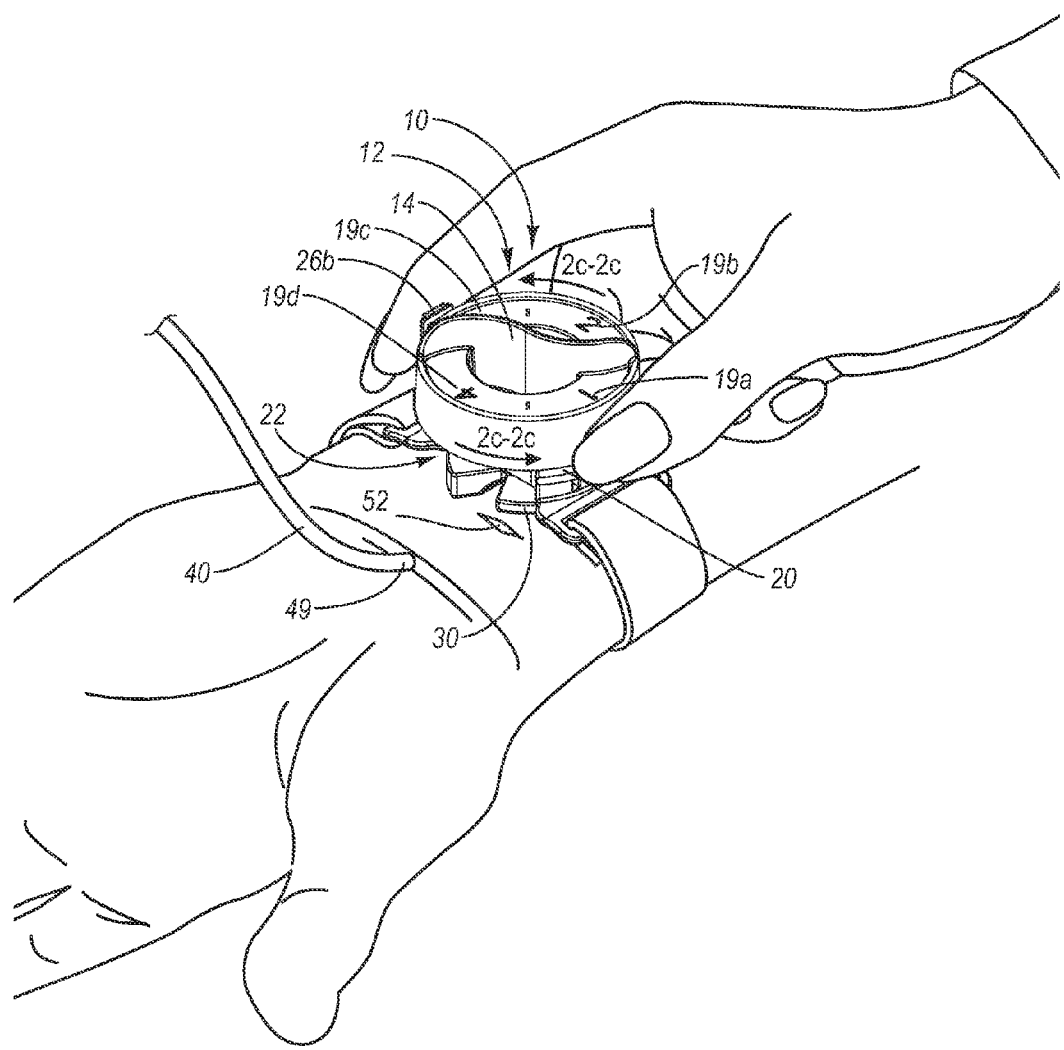
FIG. 2C is a perspective view of a radial artery compression device of FIG. 1 illustrating retraction of a compression pad of the radial artery compression device.

FIG. 2C is a perspective view of the radial artery compression device of FIG. 2A. In the illustrated embodiment, the practitioner is grasping ratchet engagement members 26a, b (see also FIG. 2B) by urging ratchet engagement members 26a, b (see also FIG. 2B) toward one another. In this manner, an internal ratchet member which prevents counter-clockwise rotational movement of rotatable member 12 is released. Once the ratchet engagement members 26a, b (see also FIG. 2B) are compressed, the practitioner can rot ate rotatable member 12 in a counter-clockwise direction indicated by directional arrows 2c-2c. As the practitioner rotates rotatable member 12 in a counter-clockwise direction, compression pad 30 is retracted back in the direction of body 20. In other words, as rotatable member 12 is rotated in the counter-clockwise direction indicated by rotational arrows 2c-2c, the distance between body 20 and compression pad 30 lessens until compression pad 30 is fully retracted into a recess of body 20.

As the amount of force provided by compression pad 30 decreases, the securement of catheter 40 within the patient's wrist is lessened. Once the compression provided by compression pad 30 is diminished to a desired extent, a practitioner can grasp catheter 40 and withdraw catheter 40 from within the patient's radial artery. In the illustrated embodiment, catheter 40 is depicted as having been withdrawn from access site 52 and from the patient's vasculature. Once the catheter tip 49 has been withdrawn from the patient's body, the practitioner can once again rotate rotatable member 12 in a clockwise direction and increase the pressurization provided by compression pad 30 on the access site 52. This provides a desired degree of hemostasis until the access site closes and heals sufficiently to prevent further bleeding of the access site subsequent to the procedure. As a result, radial artery compression device 10 can provide supplemental pressure at the catheter access point after the procedure has been completed rather than requiring a nurse, doctor, or patient from applying pressure until bleeding at the catheter access site has diminished or stopped. Additionally, the amount of pressure can be adjusted. For example, initially a greater amount of compression pressure can be provided. After an amount of time, the pressure provided by the radial artery compression device can be lessened.

Figure 3:
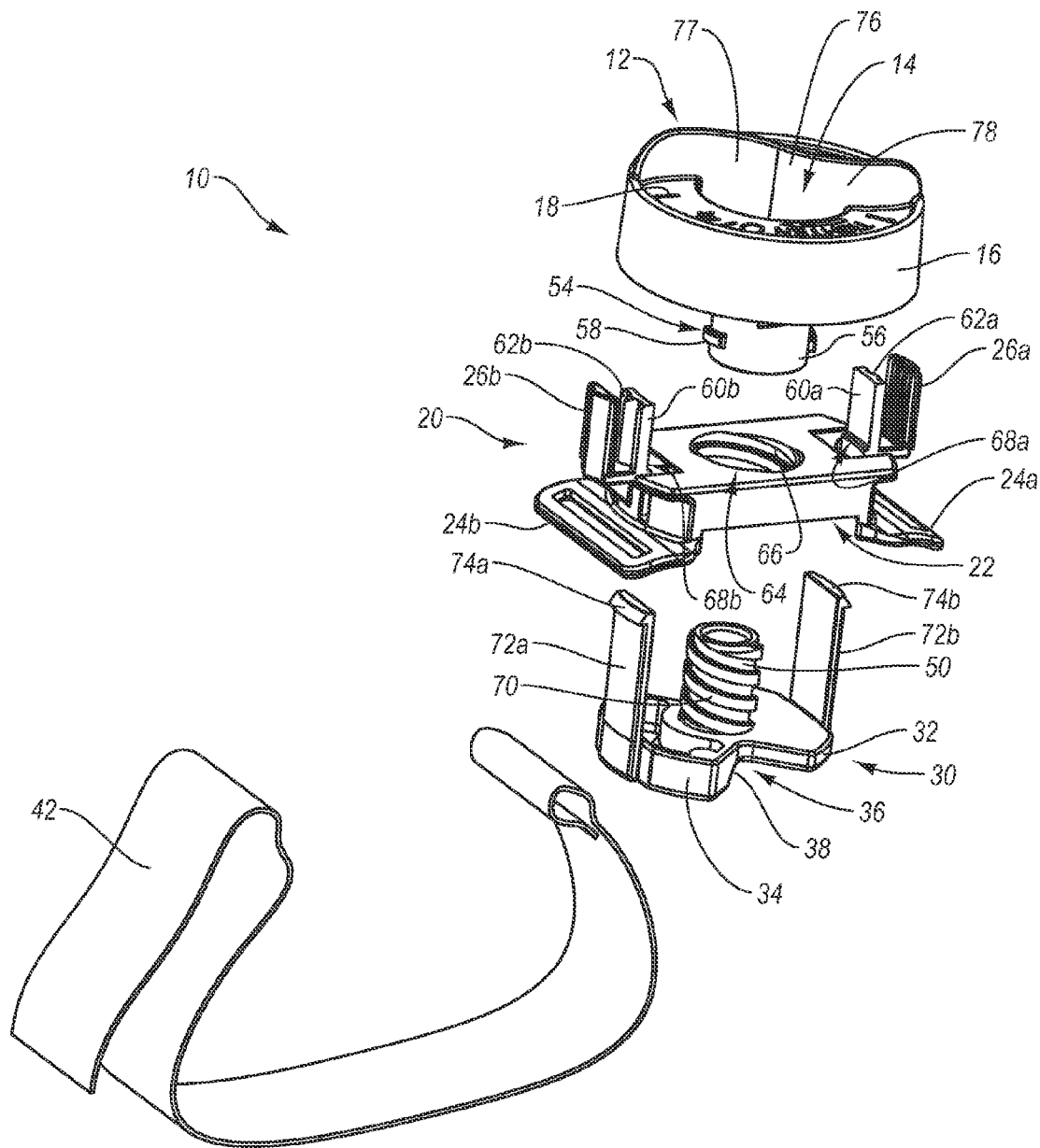
FIG. 3 is an exploded view of a radial artery compression device of FIG. 1 according to one aspect of the present invention.

FIG. 3 is a perspective exploded view of radial artery compression device 10 according to one embodiment of the present invention. In the illustrated embodiment, the threaded components of radial artery compression device 10 are depicted. Threaded shaft 50 is integrally coupled to compression pad 30. A rotatable member post 54 having threads 58 on the outside surface 56 of rotatable member post 54 is depicted. Rotatable member post 54 is integrally coupled to rotatable member 12. Additionally, a center aperture 64 of body 20 is depicted. Center aperture 64 also includes a plurality of threads 66. Center aperture 64 is adapted to engage threads 58 on the outside surface 56 of rotatable member post 54.

As a practitioner rotates rotatable member 12, threads 58 of rotatable member post 54 threadably engage threads 66 of center aperture 64. As a result, as rotatable member 12 is rotated, rotatable member 12 is axially displaced relative to body 20. Threaded shaft 50 includes threads 70 on the outside surface of threaded shaft 50. Threads 70 on the outside surface of threaded shaft 50 are adapted to engage threads positioned on the inside diameter of rotatable member post 54. The threaded engagement of threaded shaft 50 and rotatable member post 54 results in displacement of compression pad 30 relative not only to body 20, but also to rotatable member 12 pursuant to rotation of rotatable member 12. The threaded engagement of threaded shaft 50, rotatable member post 54 and body 20 results in a compounding effect of the movement of compression pad 30 during rotation of rotatable member 12.

When rotatable member 12 is rotated, cooperative engagement between rotatable member post 54 and center aperture 64 results in displacement of rotatable member 12 relative to body 20. The engagement between threaded shaft 50 and rotatable member post 54 results in displacement of compression pad 30 relative to body 20. Additionally, the engagement of threaded shaft 50 and rotatable member post 54 results in an amount of displacement of compression pad 30 relative to rotatable member 12. According to one embodiment of the present invention, a first amount of displacement between compression pad 30 and body 20 results upon a first amount of rotation of rotatable member 12. A second amount of displacement which is different than the first amount of displacement occurs between compression pad 30 and rotatable member 12 upon the same amount of rotation of rotatable member 12.

The primary and secondary threaded engagement results in a compounding effect pursuant to which rotation of rotatable member 12 results in a greater amount of displacement between compression pad 30 and body 20 than the displacement provided between rotatable member 12 and body 20 pursuant to a given amount of rotation. For exemplary purposes, according to one embodiment of the present invention, when the rotatable member is rotated one-half rotation, a change in displacement between rotatable member 12 and body 20 of approximately one-quarter inch occurs. During the one-half rotation of rotatable member 12, a change of displacement between compression pad 30 and body 20 of approximately one-half inch occurs. In other words, compression pad 30 moves approximately twice as far relative to body 20 than rotatable member 12 moves relative to body 20 during the same amount of rotation of rotatable member 12.

In the illustrated embodiment, rotation of rotatable member 12 in a clockwise direction results in movement of rotatable member 12 in the direction of body 20. The same rotation of rotatable member 12 in the clockwise direction results in a greater amount of displacement between compression pad 30 and body 20. In other words, rotation of rotatable member 12 in a clockwise direction results in downward movement of both handle member 14 and compression pad 30. Rotation of rotatable member 12 in a counter-clockwise direction results in retraction of compression pad 30 in the direction of body 20. Additionally, rotation of rotatable member 12 in a counter-clockwise direction results in a greater amount of displacement between body 20 and rotatable member 12. In other words, rotation of rotatable member 12 in a counter-clockwise direction results in upward movement of both compression pad 30 and rotatable member 12.

In the illustrated embodiment, rotatable member posts 60a, b are depicted. Rotatable member posts 60a, b include ramp surfaces 62a, b on their outward facing surfaces. Ramp surfaces 62a, b are adapted to engage ramp or notch members provided on the inside diameter of rotatable member 12. The alignment and orientation of ramp surfaces 62a, b allow rotation of rotatable member 12 in a first direction while preventing or minimizing rotation of rotatable member 12 in a second direction. When a user desires to rotate rotatable member 12 in the second direction, ramp surfaces 62a, b will inhibit such rotation. In order to effectuate rotation of rotatable member 12 in the reverse direction, the user simply grasps ratchet engagement members 26a, b and urges them in an inward direction. This results in inward lateral movement of rotatable member engagement posts 60a, b. The lateral movement of rotatable member engagement posts 60a, b causes disengagement of ramp surfaces 62a, b from the ratchet members on the inside diameter of rotatable member 12 permitting the rotational movement of rotatable member 12 in a second direction.

In the illustrated embodiment, the configuration of ramp surfaces 62a, b permits rotation of rotatable member 12 in a first direction without requiring the actuation of ratchet engagement members 26a, b. However, ramp surfaces 62a, b minimize or prevent the rotational movement of rotatable member 12 in a counter-clockwise direction absent, or in the absence of, actuation of ratchet engagement members 26a, b.

Body engagement posts 72a, b are provided in connection with compression pad 30. Body engagement posts 72a, b are integrally coupled or otherwise secured to compression pad 30. Body engagement posts 72a, b are adapted to be threaded through lateral apertures 68a, b positioned through alternative sides of body 20 and on opposing sides of center aperture 64. Body engagement posts 72a, b maintain the rotational orientation of compression pad 70 relative to the other components of radial artery compression device 10 during rotation of rotatable member 12. In this manner, a desired alignment of compression pad 30, and in particular notch 36 and step 38 of compression pad 30, can be maintained notwithstanding the rotational position of rotatable member 12. Body engagement posts 72a, b include tabs 74a, b. Tabs 74a, b are sloped structures which permit the introduction of body engagement posts 72a, b through lateral apertures 68a, b during assembly. Additionally, tabs 74a, b include a shelf member which inhibits or prevents the accidental removal or passage of body engagement posts from their cooperative engagement with body 20.

Body engagement posts 72a, b also maintain the rotational orientation of threaded shaft 50. As a result, rotation of rotatable member post 54 pursuant to rotation of rotatable member 12 results in movement of threads 58 of rotatable member post 54 in relation to threads 70 of threaded shaft 50. Rotation of rotatable member post 54 results in axial movement of threaded shaft 50 and compression pad 30 relative to rotatable member post 54. As rotatable member 12 is rotated, rotatable member post 54 also rotates. During rotation of rotatable member post 54, the rotational orientation of body 20, threads 66 of center aperture 64, compression pad 30 and threads 70 of threaded shaft 50 remains fixed. As a result, threaded shaft 50, compression pad 30, rotatable member post 54 and rotatable member 12 are displaced axially relative to body 20 pursuant to rotation of rotatable member 12 and rotatable member post 54.

The juxtaposition of rotatable member post 54 relative to center aperture 64 and threaded shaft 50 relative to rotatable member post 54 also helps to minimize rotational forces which may urge compression pad 30 to a different rotational position other than the one desired. In the illustrated embodiment, recess 22 is illustrated. Recess 22 comprises a cutout or spaced gap type member on the underside of body 20. Recess 22 is sized to receive compression pad 30 when compression pad 30 is retracted to its position closest to body 20. In other words, when compression pad 30 is fully retracted relative to body 20, all or a portion of compression pad 30 is positioned within recess 22.

In the illustrated embodiment, handle member 14 is provided in connection with rotatable member 12. The shape of handle member 14 allows a user to place a thumb and index finger on alternative sides of handle member 14 to twist rotatable member 12 in either a clockwise or counter-clockwise rotational direction. The arcuate configuration of handle member 14 creates a concave surface 77 and convex surface 78 on each lateral side of handle member 14. For example, the concave portion 77 of lateral side 76 of handle member 14 is on the opposing side of a convex portion on the other lateral side of the handle member 14. Similarly, the convex portion 78 on the lateral side 76 is on the opposing side of the concave portion of the opposing lateral side of the handle member 14. In this manner, an ergonomic and easy to grasp configuration is provided by handle member 14.

As will be appreciated by those skilled in the art, a variety of types and configurations of radial artery compression devices can be provided without departing from the scope and spirit of the present invention. For example, according to one embodiment of the present invention, a mechanism other than a ratchet engagement member is provided to secure the rotational position of the rotatable member. According to another embodiment of the present invention, a ratchet engagement member is provided only on one side of the rotatable member.

According to another embodiment of the present invention, the rotational position of the compression pad is secured relative to the body utilizing a mechanism other than the body engagement post. According to another embodiment of the present invention, rotation of the rotatable member results in movement of the compression pad utilizing a single set of threads. According to yet another embodiment of the present invention, rotation of the rotatable member only results in movement of the compression pad relative to the body and does not cause movement of the rotatable member relative to the body.

Figure 4A:
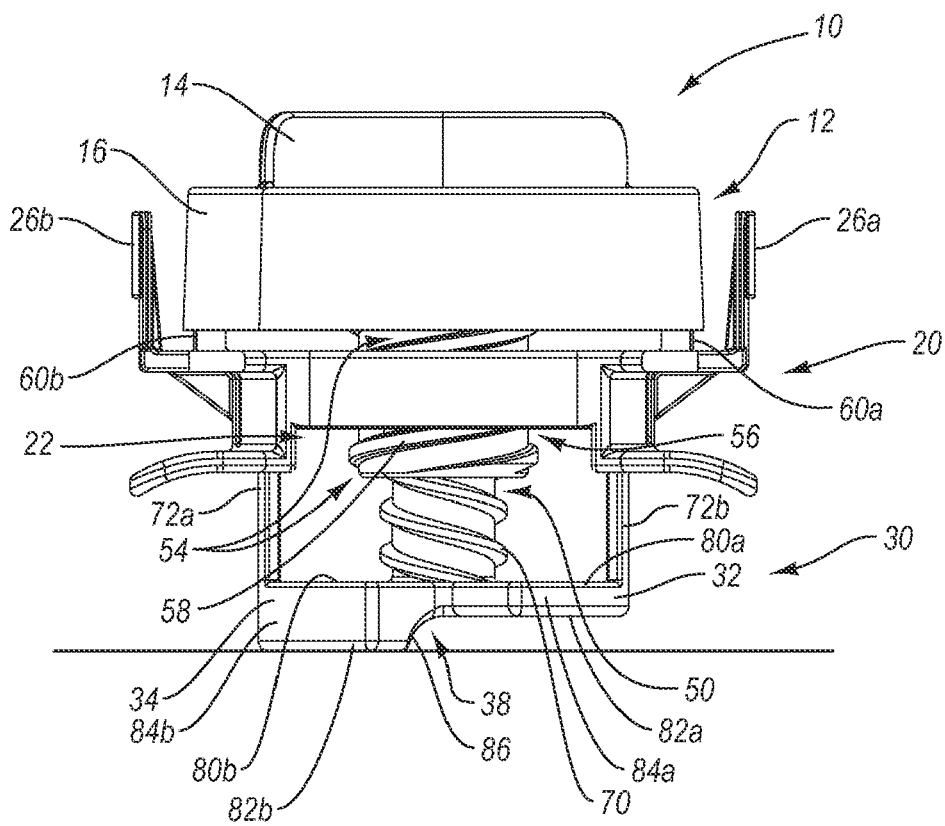
FIG. 4A is side view of a radial compression device of FIG. 1 illustrating the compression pad in an extended position according to one aspect of the present invention.

FIG. 4A is a side view of radial artery compression device 10 of FIG. 1 according to one embodiment of the present invention. In the illustrated embodiment, compression pad 30 is illustrated in a fully extended position. When compression pad 30 is in a fully extended position, the displacement between compression pad 30 and body 20 is maximized. Additionally, when compression pad 30 is in a fully extended position, rotatable member 12 is positioned at a displacement that is closer to body 20 than at any other rotational position of rotatable member 12.

Rotatable member engagement posts 60a, b are positioned in cooperative engagement with the inside diameter of rotatable member 12. When a user desires to rotate rotatable member 12 in a counter-clockwise direction to permit the retraction of compression pad 30, a user simply depresses ratchet engagement members 26a, b toward one another. Depressing of ratchet engagement members 26a, b results in manipulation of a portion of body 20 coextensive with rotatable member engagement posts 60a, b. As a result, the cooperative engagement provided in connection with ramp surfaces 62a, b (see FIG. 3) is broken permitting rotational movement of rotatable member 12 in a counter-clockwise direction.

In the illustrated embodiment, the juxtaposition of threaded shaft 50 relative to rotatable member post 54 is depicted. Threads 70 of threaded shaft 50 are cooperatively engaged with threads that are positioned on the inside diameter of rotatable member post 54. As a result, when rotatable member 12 is rotated, rotation of rotatable member post 54 results in axial movement of compression pad 30 due to the interaction between threads 70 of threaded shaft 50 and the threads on the inside diameter of rotatable member post 54. Additionally, the engagement between threads 58 on the outside surface 56 of rotatable member post 54 results in movement of rotatable member post 54 relative to body 20. Threads 58 of rotatable member post 54 cooperatively engage threads 66 of center aperture 64 (see FIG. 3). As a result, movement of compression pad 30 results not only from the engagement of threaded shaft 50 with rotatable member post 54, but also the cooperative engagement of rotatable member post 54 with body 20. The engagement of the components of threaded shaft 50, rotatable member post 54 and center aperture 64 cause a compounding of the axial displacement of compression pad such that a given amount of axial displacement of rotatable member 12 relative to body 20 results in a greater amount of axial displacement of compression pad 30 relative to body 20 than would be provided by a single threaded interaction.

Compression pad 30 includes a first portion 32 and a second portion 34. First portion 32 is positioned on one side of step 38 and second portion 34 is positioned on the opposing side of step 38. First portion 32 includes an interior surface 80a and a contact surface 82a. Second portion 34 includes an interior surface 80b and a contact surface 82b. Additionally, first portion 32 includes a sidewall 84a and second portion 34 includes a sidewall 84b. In the illustrated embodiment, the displacement between interior surface 80a and contact surface 82a has a smaller amount of displacement than the displacement between interior surface 80b and contact surface 82b of second portion 34. In other words, sidewall 84a of first portion 32 is smaller or has a smaller height than the height of sidewall 84b of second portion 34. The differing heights of sidewall 84a and 84b are adapted such that the elevation of contact surface 82a of first portion 32 is different from the elevation of contact surface 82b of second portion 34.

The differing elevations of contact surface 82a and 82b allows the contact surfaces of compression pad 30 to conform to a patient's wrist. As a result, contact surface 82b of second portion 34 can be positioned on the outside of the patient's wrist while contact surface 82a of first portion 32 can be positioned toward the inner part of the patient's wrist. In this manner, a consistent and desired amount of contact between most or all of compression pad 30 can be maintained relative to the patient's wrist, notwithstanding the elevational changes and the physiological features of a typical patient's wrist.

Step 38 is adapted to be positioned over the patient's artery. Step 38 includes a contact surface 86 which runs along the length of step 38. In the illustrated embodiment, contact surface 86 has a curvilinear or arcuate configuration which is adapted to somewhat conform to the curvilinear outside diameter of a typical catheter or to the rounded configuration of the outside diameter of the patient's radial artery. In this manner, when a catheter is positioned within the patient's radial artery, a desired cooperative contact can sandwich the outside diameter of the patient's radial artery between the catheter and the patient's body tissues as a result of the compression provided by the contact surface 86 of step 38.

In the illustrated embodiment, when compression pad 30 is positioned at its fully extended position, a maximum amount of displacement between contact surface 82a and contact surface 82b is provided relative to the underside of recess 22. In other words, when compression pad 30 is in its fully extended position, contact surfaces 82a and 82b are also positioned at their furthest displacement relative to body 20. As a result, when compression pad 30 is at a fully extended position a maximum amount of compression can be provided when radial artery compression device 10 is secured to a patient's wrist.

As will be appreciated by those skilled in the art, a variety of types and configurations of radial artery compression devices can be provided without departing from the scope and spirit of the present invention. For example, according to one embodiment of the present invention, the extension of the compression pad is the result not only of the rotation of the rotatable member, but also of other operating components of the radial artery compression device. According to another embodiment of the present invention, the extension of the compression pad is only one of two or more components that are utilized to exert pressure on a patient's radial artery or other physiological feature. According to another embodiment of the present invention, the compression pad has a first rigid component and a second flexible component which cooperatively engage the patient's radial artery or catheter. According to yet another embodiment of the present invention, the shape, configuration or material properties of the relief surface or contact surfaces of the compression pad can vary.

Figure 4B:
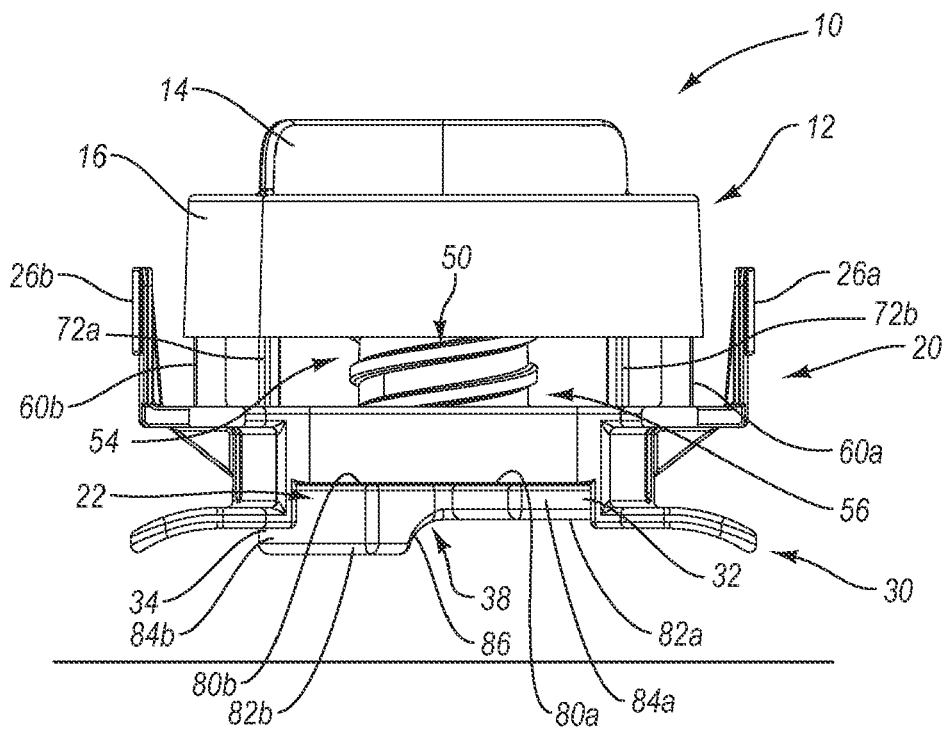
FIG. 4B is a side view of a radial compression device of FIG. 4A illustrating the compression pad in the retracted position according to one aspect of the present invention.

FIG. 4B is a side view of the radial artery compression device 10 illustrating compression pad 30 in a fully retracted position. In the illustrated embodiment, when compression pad 30 is in a fully retracted position, rotatable member 12 is positioned at a maximum amount of axial displacement relative to body 20. When compression pad 30 is in a fully retracted position, compression pad 30 is fully or partially retracted within recess 22. In the illustrated embodiment, it can be seen that when compression pad 30 is in a fully retracted position, body engagement posts 72a, b extend above the upper surface of body 20.

As will be appreciated by those skilled in the art, to move compression pad 30 from the fully extended position depicted in FIG. 4A, to the fully retracted position depicted in FIG. 4B, the user rotates rotatable member 12 in a counter-clockwise direction. To rotate the rotatable member 12 in a counter-clockwise direction, the user actuates ratchet engagement members 26a, b disengaging rotatable member engagement posts 60a, b relative to rotatable member 12 and permitting rotation of rotatable member in a counter-clockwise direction. As the user rotates rotatable member 12 in a counter-clockwise direction, compression pad 30 is retracted in the direction of body 20. The configuration of rotatable member 12 and the other components of radial artery compression 10 device allows for varying amounts of displacement between compression pad 30 and body 20. In this manner, varying degrees of compression can be provided by radial artery compression device 10, depending on the particular requirements of the procedure being performed and/or how tightly radial artery compression device 10 is secured relative to the patient. Additionally, the practitioner can rotate rotatable member 12 to incrementally change the degree of extension of compression pad 30 throughout the course of the procedure to adjust the amount of compression provided by radial artery compression device 10.

In the illustrated embodiment, interior surfaces 80a, b are positioned directly adjacent or in contact with body 20. Additionally, all or a part of sidewalls 84a, b are retracted within recess 22. As will be appreciated by those skilled in the art, compression pad 30 can be fully retracted in recess 22 at the beginning of a procedure before compression pad 30 has been actuated. Similarly, compression pad 30 can be fully retracted into recess 22 at the end of a procedure after a catheter has been withdrawn from the patient. Compression pad 30 can also be retracted into recess 22 at any point during the course of the procedure when a practitioner desires to reposition the radial artery compression device or otherwise release pressure from the patient's vasculature.

In the illustrated embodiment, when compression pad 30 is retracted into recess 22, rotatable member post 54 has been rotated such that the bottom of rotatable member post 54 is fully retracted within body 20. Additionally, the portion of threaded shaft 50 positioned adjacent compression pad 30 has been fully retracted to within body 20. As a result, when compression pad 30 is fully retracted within body 20, the overall elevational profile from the top of handle member 14 to the bottom of compression pad 30 is at its smallest. Or in other words, the displacement between the top of handle member 14 and the bottom of compression pad 30 is at its smallest when compression pad 30 is fully retracted to within body 20. In contrast, when compression pad 30 is at its fully extended position, the displacement between the top of handle member 14 and the bottom of compression pad 30 is at its greatest displacement. The relative change in displacement between the top of handle member 14 and the bottom of compression pad 30 at the different rotational positions of rotatable member 12 is a result of the compound movement of compression pad 30 relative to body 20 provided by the multiple threaded engagements between threaded shaft 50, rotatable member post 54, and center aperture 64 (see FIG. 3).

In the illustrated embodiment the underside of rotatable member 12 is configured to accommodate the top of body engagement post 72a, b. This permits the desired axial movement of body engagement post 72a, b as compression pad 30 moves in the direction of rotatable member 12 and in spite of the compounded axial displacement of compression pad 30 resulting from the cooperative engagement of threaded shaft 50, rotatable member post 54 and center aperture 64.

As will be appreciated by those skilled in the art, a variety of types and configurations of radial artery compression devices can be provided. According to one embodiment of the present invention, a single threaded engagement is provided between the components of the radial artery compression device. According to another embodiment of the present invention, four or more threaded engagements are provided in connection with the components of the radial artery compression device to provide further compounding of the axial movement of one or more components of the radial artery compression device. According to another embodiment of the present invention, the rotational position of the compression pad is maintained in place utilizing a mechanism other than body engagement post. According to yet another embodiment of the present invention, the body engagement post comprises a uniform outer wall around most or all of the outer circumference of the compression pad. According to yet another embodiment of the present invention, movement of the compression pad is provided in a linear fashion rather than a compounding fashion as depicted in FIG. 4B.

Figure 5:
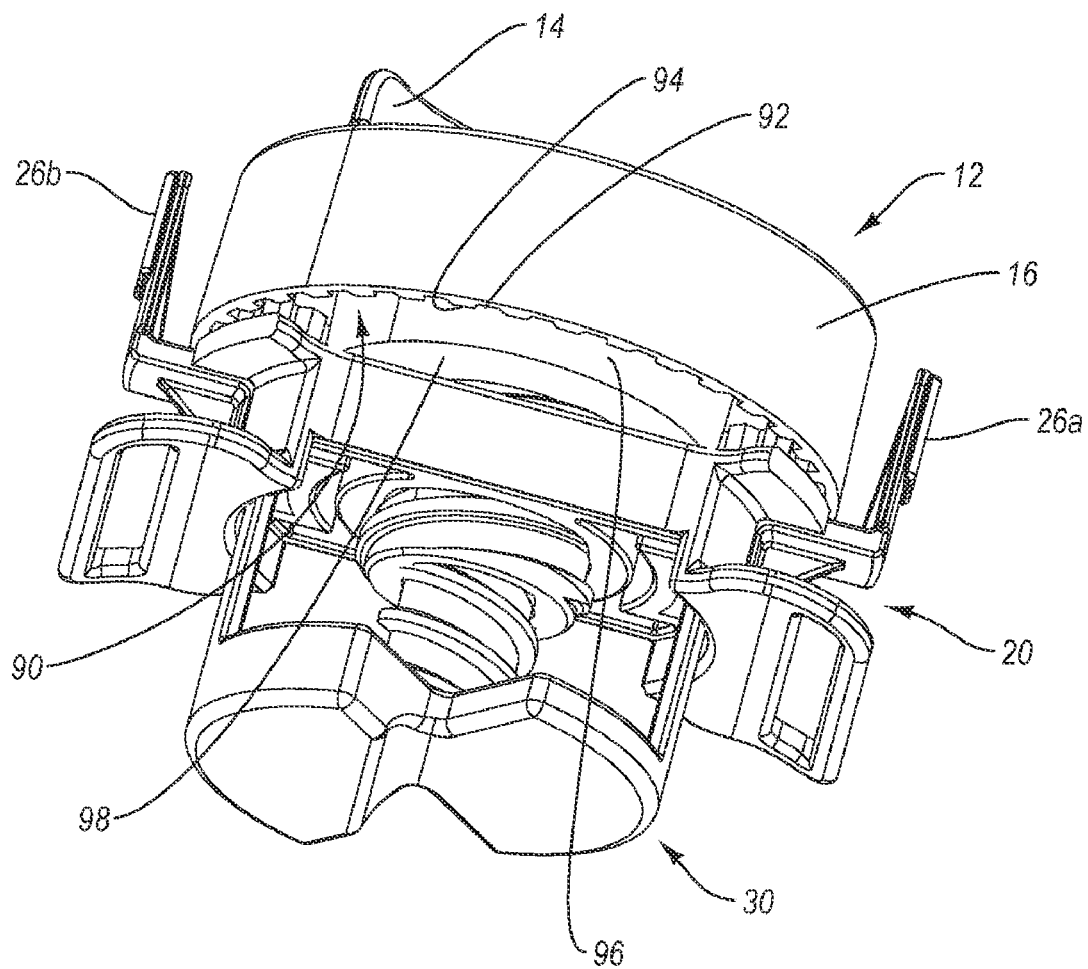
FIG. 5 is a bottom perspective view of a radial artery compression device of FIG. 1 illustrating the ratcheting mechanism of the radial artery compression device according to one aspect of the present invention.

FIG. 5 is a bottom perspective view of the radial artery compression device of the present invention. In the illustrated embodiment, the internal configuration of the rotatable member 12 can be seen. Rotatable member 12 includes a recess 90 which is positioned on an inner diameter of sidewall 16. Recess 90 is adapted to accommodate rotatable member engagement post 60a, b (see FIG. 3).

Recess 90 is coextensive with an inside diameter of sidewall 92, ramps 94, and an interior wall 96. In the illustrated embodiment, the inside diameter of sidewall 92 includes a plurality of ramps 94. Ramps 94 are one example of a ratchet mechanism which are adapted to engage ramps surfaces 62a, b of rotatable member engagement post 60a, b (see FIG. 3). The configuration of ramps 94 permits rotational movement of rotatable member 12 in a first direction while controlling rotation of rotatable member 12 in a second direction. In other words, the practitioner can rotate rotatable member 12 in one direction without actuating ratchet engagement members 26a, b. To freely rotate rotatable member 12 in a second direction, the practitioner actuates ratchet engagement members 26a, b. For example, according to one embodiment of the present invention, the practitioner is allowed to rotate rotatable member 12 in a clockwise direction as depicted in FIG. 2B without actuating ratchet engagement members 26a, b. However, the practitioner actuates ratchet engagement members 26a, b in order to rotate rotatable member 12 in a second direction as depicted in FIG. 2C.

In the illustrated embodiment, rotatable member 12 includes a bottom contact surface 98. When rotatable member 12 is rotated such that compression pad 30 is fully extended, bottom contact surface 98 is positioned adjacent to and in contact with body 20. When the practitioner rotates rotatable member 12 in a second direction such that compression pad 30 is fully retracted into body 20 as depicted in FIG. 4B, a desired amount of displacement is provided between bottom contact surface 98 and body 20. In other words, when compression pad 30 is fully retracted, a greater amount of displacement is provided between compression pad 30 and body 20 than is provided between rotatable member 12 and body 20. When compression pad 30 is fully retracted, a greater amount of displacement is provided between rotatable member 12 and body 20 than is provided between compression pad 30 and body 20.

As will be appreciated by those skilled in the art, a variety of types and configurations of radial artery compression devices can be provided without departing from the scope and spirit of the present invention. For example, in one embodiment only the handle member of the radial artery compression device rotates. In this embodiment, the sidewall remains fixed in its rotational orientation while interior components rotate pursuant to rotation or other actuation of a handle member, button or other actuation mechanism.

According to one aspect of the present invention, ramps 94 may be positioned on interior wall 96 so as to permit rotation of the handle member 14 in a first direction but to prevent rotation of the handle member 14 in a second direction. Rotatable member engagement post 60a, b (see FIG. 4B) are directed to engage ramps 94 which would be positioned on the interior wall 96 associated with handle member 14. According to another aspect of the present invention, actuation of ratchet engagement member 26a not only biases the portion of body 20 associated with rotatable member engagement posts 60a, b (see FIG. 4B), but causes the mechanical movement of the post pursuant to secondary mechanical members such as a spring, a leaf spring, biasing member or other actuatable components.

Figure 6A:
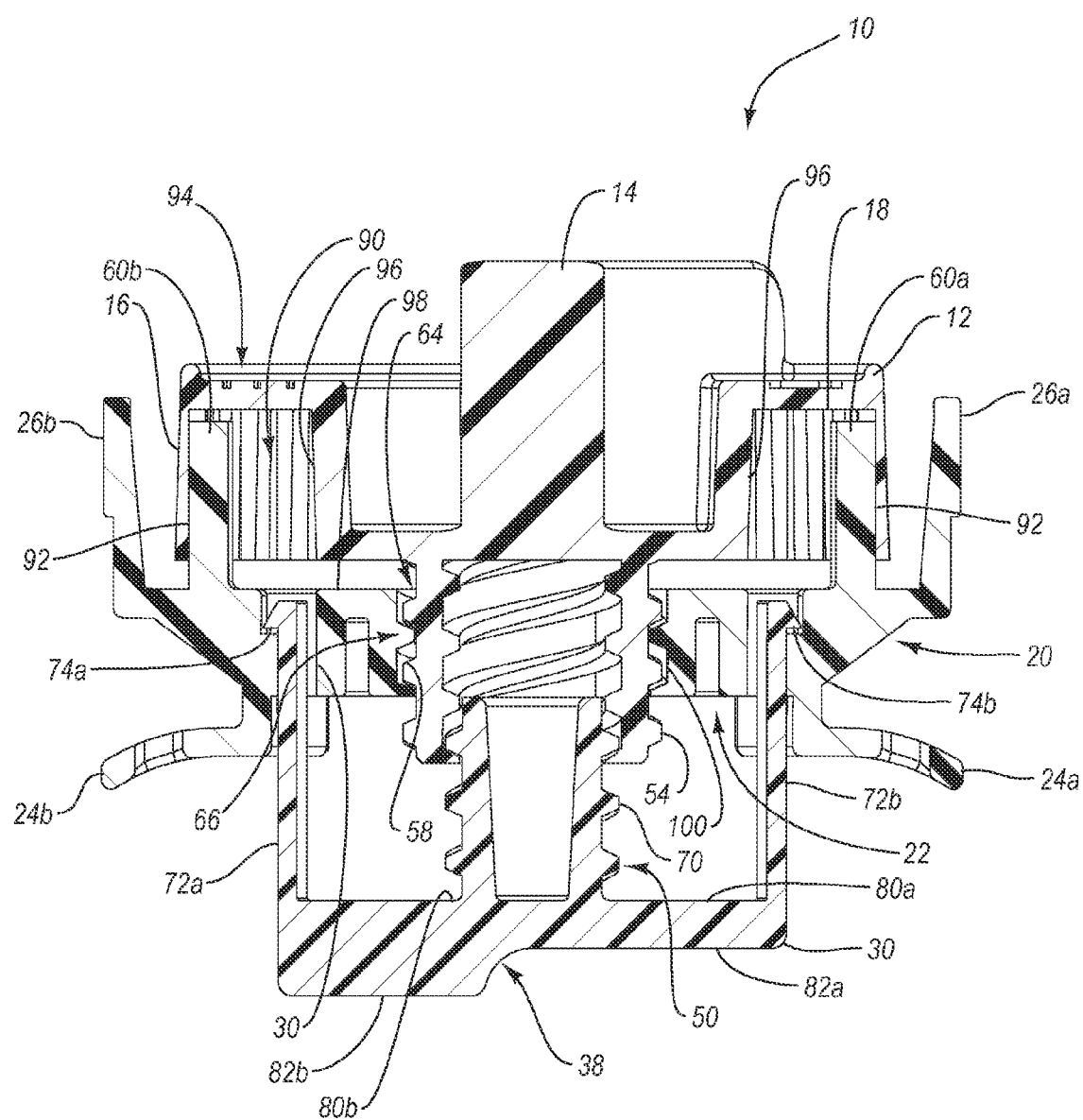
FIG. 6A is a cross-sectional view of a radial artery compression device of FIG. 1 illustrating the compression pad in an extended position according to one aspect of the present invention.

FIG. 6A is a side cutaway view of radial artery compression device 10 according to one embodiment of the present invention. In the illustrated embodiment, threads 66 of center aperture 64 are illustrated and compression pad 30 is shown in a fully extended position. When compression pad 30 is in a fully extended position, interior surfaces 80a, b are positioned a given amount of displacement from the underside of recess 22. In other words, a maximum amount of displacement between contact surfaces 82a, b and body 20 is provided when compression pad 30 is in a fully extended position. Additionally, only the upper portion of body engagement posts 72a, b are positioned within recess 90 of rotatable member 12.

When compression pad 30 is in a fully extended position, bottom contact surface 98 of rotatable member 12 is positioned in contact with body 20. Ramps 94 on the inside diameter of sidewall 92 cooperatively the engage ramp surfaces of rotatable member engagement posts 60a, b. The cooperative engagement between the ramp surfaces of rotatable engagement posts 60a, b and ramps 94 permit rotation of rotatable member 12 until compression pad 30 is fully extended. Once compression pad 30 is in a partially or fully extended position, engagement between the ramp surfaces of rotatable engagement posts 60a, b and ramp 94 prevent or minimize rotation of rotatable member 12 in a rearward direction unless the practitioner depresses ratchet engagement members 26a, b.

As the practitioner rotates rotatable member 12, rotatable member post 54 is also rotated as a result of the integral coupling between rotatable member 12 and rotatable member post 54. As rotatable member post 54 is rotated, threads 58 of rotatable member post 54 engage threads 66 of center aperture 64. The threaded engagement between threads 58 and 66 displaces rotatable member 12 relative to body 20. Additionally, rotation of rotatable member 12 and rotatable member post 54 results in engagement of threads 70 by threads 100 on the inside diameter of rotatable member post 54. In this manner, rotation of rotatable member 12 provides interactive forces which result in the axial displacement of compression pad 30 relative to rotatable member 12. Axial displacement of rotatable member 12 relative to compression pad 30 is a result of the interaction between threads on the inside diameter of center aperture 64, threads on the outside diameter of rotatable member post 54, threads on the inside diameter of rotatable member post 54, and threads on the outside diameter of threaded shaft 50. The cooperative engagement of these threads results in a compounding of the axial movement of compression pad 30 relative to body 20.

In the illustrated embodiment, rotatable member post is positioned such that the portion of rotatable member post 54 adjacent rotatable member 12 has been substantially advanced into body 20. The bottom or distal most extent of rotatable member post 54 extends below body 20 such that the distal extent of rotatable member post extends below recess 22 and wrist strap securement members 24a, b. Threaded shaft 50 has been extended a given amount such that the portion of threaded shaft 50 which is positioned adjacent to compression pad 30 extends outside of rotatable member post 54. The cooperative engagement of threaded shaft 50, rotatable member post 54 and center aperture 64, results in compounding of the axial movement of compression pad 30 relative to body 20 when rotatable member 12 is rotated by a practitioner.

Figure 6B:
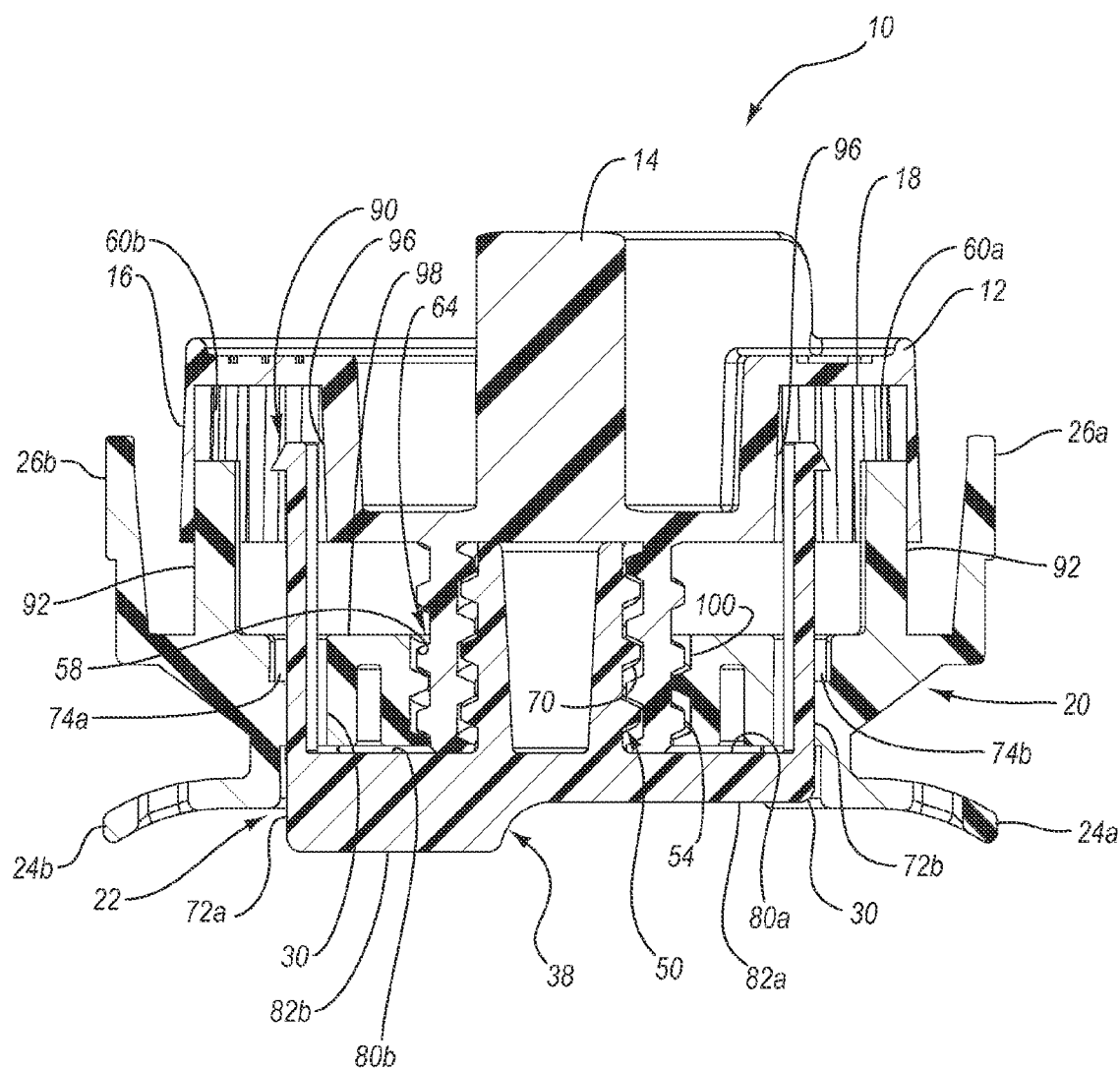
FIG. 6B is a cross-sectional view of a radial artery compression device of FIG. 6A illustrating the compression pad in a retracted position according to one aspect of the present invention.

FIG. 6B illustrates radial artery compression device 10 in which compression pad 30 is in a fully retracted position. In the illustrated embodiment, when compression pad 30 is in a fully retracted position, contact surface 82a is aligned with the portion of wrist strap securement member 24a positioned adjacent compression pad 30. In other words, the portion of compression pad 30 positioned adjacent wrist strap securement member 24a is fully retracted to within recess 22. Contact surface 82b is positioned adjacent wrist strap securement member 24b. Contact surface 82b extends a certain amount of displacement below wrist strap securement member 24b. This is due to the fact that contact surface 82b has a lower elevation than contact surface 82a. It will be appreciated that the configuration of the contact surfaces of compression pad 30 and the amount to which compression pad 30 is withdrawn into a recess of body 20 can vary depending on the size of the recess, the thickness of the compression pad, or other variables related to the components of the radial artery compression device that can be selected according to the particular requirements of a compression procedure to be performed.

In the illustrated embodiment, when compression pad 30 is fully retracted within recess 22, rotatable member 12 is positioned at its greatest displacement from body 20. Bottom contact surface 98 is positioned at a given amount of displacement from the portion of body 20 positioned opposite bottom contact surface 98. Body engagement posts 72a, b are fully retracted such that a substantial portion of body engagement posts 72a, b extend above body 20. When compression pad 30 is fully retracted to within body 20, the portion of body engagement posts 72a, b associated with tab 74a, b extend higher than rotatable member engagement posts 60a, b. As a result, a portion of body engagement posts 72a, b are positioned within recess 90.

In the illustrated embodiment, a substantial portion of rotatable post member 54 is positioned above body 20. Additionally, the bottom extremity of rotatable member post 54 is retracted such that it is positioned within body 20. Similarly, when compression pad 30 is fully retracted to within body 20, threaded shaft 50 is retracted to a position within body 20 such that the portion of threaded shaft 50 adjacent compression pad 30 has been retracted to within body 20 while the upper extremity of threaded shaft 50 extends above body 20. In the depicted configuration, the entire portion of threaded shaft 50 is positioned within rotatable member post 54. In other words, the upper extent of the threaded shaft 50 and the lower extent of the threaded shaft 50 are positioned such that substantially the entire length of the threaded shaft 50 is positioned within the inner cavity of the rotatable member post 54. Rotatable member post 54 is an example of a first threaded shaft. Threaded shaft 50 is an example of a secondary threaded shaft.

In the illustrated embodiment, rotatable member 12 has been displaced relative to body 20. In other words, a determined amount of displacement is provided between rotatable member 12 and body 20 when compression pad 30 is fully retracted to within body 20. As a result, only the bottom portion of inside diameter of sidewall 92 contacts ramp surfaces of rotatable member engagement post 60*a*, *b*. This is in contrast to the engagement of rotatable member engagement post 60*a*, *b* with substantially the entire length of the inside diameter of sidewall 92 when compression pad is fully extended as depicted in FIG. 6A.

As will be appreciated by those skilled in the art, of a variety of types and configurations of the internal components of the radial artery compression device can be utilized without departing from the scope and spirit of the present invention. For example, according to one embodiment of the present invention, the threaded engagement between the components associated with the compression pad, the body, and the rotatable member can occur on the outside diameter of those components rather than internally or on an inside radius of the rotatable member. According to another embodiment of the present invention, the threaded shaft associated with the rotatable member can be placed on the inside diameter while the rotatable member associated with the compression pad can be positioned on the outside of the threaded member of the rotatable member.

Figure 7:
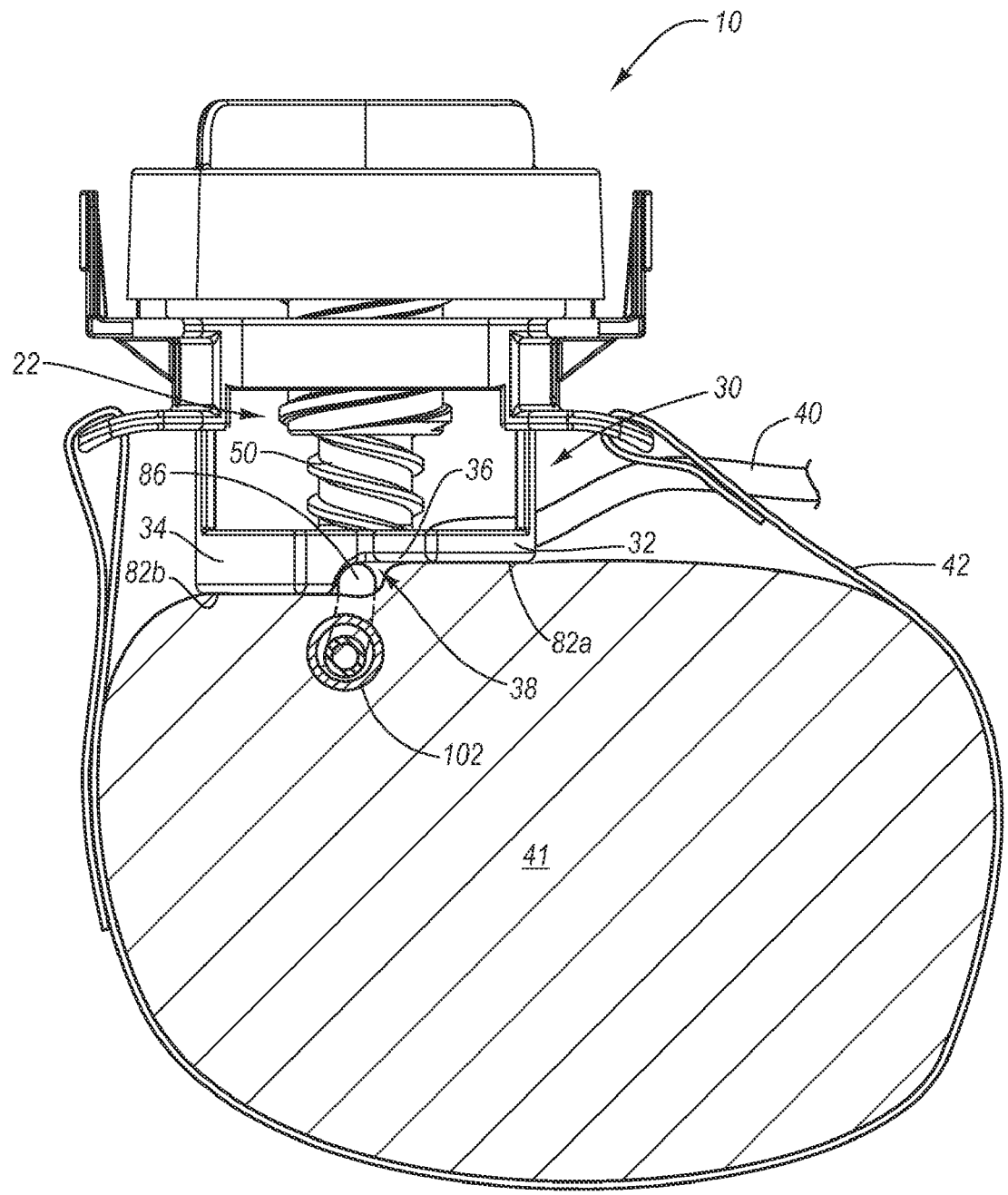
FIG. 7 is a cross-sectional view of a radial artery compression device illustrating the manner in which the compression pad secures the catheter within the radial artery of a patient according to one aspect of the present invention.

FIG. 7 is a perspective view of a patient's radial artery 102 according to one aspect of the present invention. In the illustrated embodiment, a cross-section of the patient's wrist 41 is depicted. The cross-section of the patient's wrist shows the approximate position of a catheter threaded through radial artery 102 of the patient. Radial artery 102 has an outside diameter which is substantially circumferential in nature such that the portion of radial artery 102, which is positioned to be in contact with contact surface 86 of step 38, largely conforms to the arcuate configuration of contact surface 86 of step 38.

A catheter 40 is positioned within radial artery 102 of the patient. Compression provided by compression pad 30 ensures that a desired amount of pressure is provided on radial artery 102. As a result, the inner diameter of radial artery 102 is positioned directly adjacent to and in contact with the outside diameter of catheter 40. In this manner, the tissue surrounding radial artery 102 provides sufficient contact between the outside diameter of catheter 40 and in the inside diameter of radial artery 102 to provide a desired degree of hemostasis so as to prevent bleeding or the leakage of fluid at the radial artery access site.

In the illustrated embodiment, the alignment of notch 36 relative to catheter 40 is depicted. Notch 36 enables positioning of compression pad 30 such that the radial artery access site is positioned directly below threaded shaft 50. Aligning the radial artery access site directly below threaded shaft 50 allows the compressive or axial forces provided by threaded shaft 50 to be applied directly to the radial artery access site without interruption from catheter 40. In other words, compression pad 30 can apply pressure to the patient without catheter 40 being threaded underneath a contact surface of compression pad 30 on the outside radius of compression pad 30. In this manner, the catheter 40 can be threaded through notch 36 to a more central portion of compression pad 30 such that catheter 40 does not result in obstruction or tilting of compression pad 30. As a result, direct pressure can be applied to the radial artery catheter access site by the portion of compression pad 30 associated with threaded shaft 50.

Figure 8:
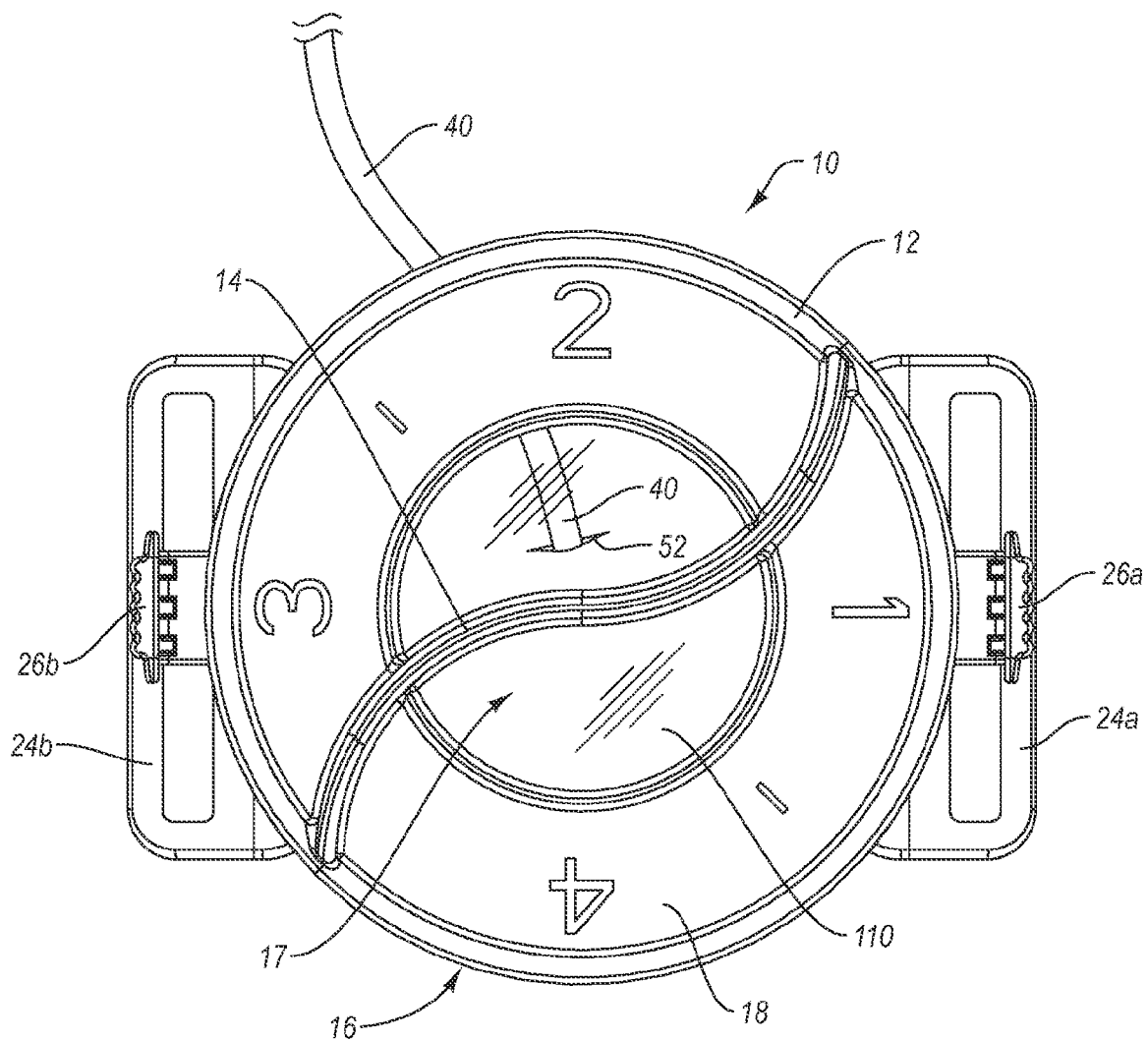
FIG. 8 is a top perspective view of a radial artery compression device according to one aspect of the present invention.

FIG. 8 is a top perspective view of a radial artery compression device 10 according to one embodiment of the present invention. In the illustrated embodiment, rotatable member 12 of radial artery compression device 10 provides visual access to the access site 52 of catheter 40. In this manner, a practitioner can approximately visualize the juxtaposition of radial artery compression device 10 relative to access site 52.

In the depicted embodiment, rotatable member 12 includes a central void 17. Central void 17 comprises a recess portion adjacent handle member 14. Central void 17 is intersected by the arcuate configuration of handle member 14. In other words, handle member 14 extends from one lateral side of central void 17 to the opposing lateral side of central void 17. In this manner, a recess is provided relative to upper face 18 of rotatable member 12. Handle member 14 can extend from an elevation which extends above upper face 18 to a position within central void which extends below upper face 18. The resultant hemispherical type voids on either lateral side of handle member 14 created by the juxtaposition of central void 17 and handle member 14 can receive the finger or thumb to grasp handle member 14 and cause rotation of rotatable member 12.

A floor surface 110 is provided in connection with central void 17. Floor surface 110 is transparent, translucent or otherwise less than opaque allowing a practitioner to see access site 52, catheter 40, or other objects or surfaces positioned on the underside of radial artery compression device 10. In this manner, a practitioner can ascertain the juxtaposition of radial artery compression device 10 relative to the patient's wrist, catheter 40, access site 52 or another object or surface. The practitioner can thus adjust the positioning of the compression pad or components of the compression pad relative to the access site 52. As will be appreciated by those skilled in the art, in order for a practitioner to be able to visualize the access site, other components of radial artery compression device may also be comprised of a clear, transparent, translucent or otherwise visually transductive material. For example, the compression pad, rotatable member post and any one or more components of the radial artery compression device 10 may be formed of a transparent or translucent material. According to another embodiment of the present invention a plurality of components or all of the components of the radial artery compression device are formed of a visually transductive material. Floor surface 110 is one example of a viewing window.

As will be appreciated by those skilled in the art, a variety of types and configurations of compression devices can be provided without departing from the scope and spirit of the present invention. For example, according to one embodiment of the present invention, a cavity or oversized recess can be provided in place of a notch on the compression pad to allow for clearance of the catheter from the bottom of the radial artery compression device. According to another embodiment of the present invention, the step has a shape other than an arcuate, radius, or circumferential contact surface which is adapted to provide a desired contact between the compression pad and the patient. According to another embodiment of the present invention, the radial artery compression device is a compression device utilized with a portion of the patient's body other than the radial artery. For example, in one embodiment of the present invention, the compression device comprises a femoral compression device which is sized and shaped to be positioned over and provide pressure to a patient's femoral artery. According to another embodiment of the present invention, the compression device is adapted to provide pressure both during the course of a procedure and upon completion of a procedure. According to yet another embodiment of the present invention, the compression device is adapted to be utilized with a plurality of compression pads which can be positioned on opposing sides of a patient's limb, adjacent multiple access sites, as desired by the practitioner, or as required by particular aspects of the procedure to be performed.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A radial artery compression device, the radial artery compression device adapted to allow a user to provide varying degrees of pressurization against a patient's radial artery to maintain a desired degree of hemostasis at a percutaneous access site, the radial artery compression device comprising:
   a body;
   a rotatable member positioned adjacent the body such that the rotatable member can be rotated relative to the body;
   a compression pad operably coupled to the rotatable member;
   a threaded shaft formed of rigid material and disposed through the body, the threaded shaft being positioned between the body and the compression pad, the threaded shaft configured to move the compression pad with respect to the body as the rotatable member is rotated relative to the body such that rotation of the rotatable member does not affect the rotational orientation of the compression pad;
   a securement member adapted to secure the position of the body relative to the portion of a patient's wrist corresponding with the radial artery, such that rotation of the rotatable member in a first direction is adapted to increase the amount of compression applied to the radial artery by the compression pad, and rotation of the rotatable member in a second direction is adapted to decrease the amount of compression applied by the radial artery to the compression pad; and
   a viewing window positioned within a central void of the rotatable member.

2. The radial artery compression device of claim 1, further comprising a secondary threaded shaft.

3. The radial artery compression device of claim 2, wherein the secondary threaded shaft is integrally coupled to the compression pad.

4. The radial artery compression device of claim 2, wherein the secondary threaded shaft threadably engages the threaded shaft.

5. The radial artery compression device of claim 4, wherein the threaded shaft includes threads on the outside diameter of a wall of the threaded shaft and threads on the inside diameter of a wall of the threaded shaft.

6. The radial artery compression device of claim 5, wherein the secondary threaded shaft engages the threads on the inside diameter of the wall of the threaded shaft.

7. The radial artery compression device of claim 5, wherein the threads on the outside diameter of the wall of the threaded shaft threadably engage the body.

8. The radial artery compression device of claim 1, wherein the threaded shaft is securely coupled to the rotatable member such that rotation of the rotatable member causes rotation of the threaded shaft.

9. The radial artery compression device of claim 1, further comprising body engagement posts secured to the compression pad to secure the rotational orientation of the compression pad during rotation of the rotatable member.

10. A radial artery compression device comprising:
    a body;
    a rotatable member positioned adjacent the body such that the rotatable member can be rotated relative to the body;
    a compression pad comprising a threaded member;
    a threaded shaft formed of rigid material and disposed through the body, the threaded shaft being positioned between the body and the compression pad, the threaded shaft configured to move the compression pad with respect to the body as the rotatable member is rotated relative to the body;
    a rotational securement component adapted to allow a practitioner to increase the amount of compression provided by the compression pad and to minimize the inadvertent or undesired removal of the desired degree of compression during the course of a procedure; and
    wherein the threaded member of the compression pad is threadably engaged by the threaded shaft.

11. The radial artery compression device of claim 10, wherein the user actuates a component of the rotational securement component to lessen the amount of compression provided by the compression pad.

12. The radial artery compression device of claim 10, wherein the rotational securement component controls rotation of the rotatable member.

13. The radial artery compression device of claim 12, wherein the rotational securement component permits rotation of the rotatable member in a first direction but controls rotation of the rotatable member in a second direction.

14. The radial artery compression device of claim 13, wherein the rotational securement component comprises a rotatable member securement device having a ratchet mechanism which permits rotation of the rotatable member in a first direction but controls rotation of the rotatable member in a second direction.

15. The radial artery compression device of claim 14, wherein rotatable member securement device comprises ratchet engagement members which permit rotation of the rotatable member in a first direction but control rotation of the rotatable member in a second direction such that a user actuates the ratchet engagement members to permit rotation of the rotatable member in the second direction.

16. A radial artery compression device, the radial artery compression device adapted to allow a user to provide varying degrees of pressurization against a patient's radial artery to maintain a desired degree of hemostasis at a percutaneous access site, the radial artery compression device comprising:
    a body;
    a rotatable member positioned adjacent the body such that the rotatable member can be rotated relative to the body;
    a compression pad operably linked to the rotatable member;
    a first shaft being positioned between the rotatable member and the compression pad, the first shaft threadably engaging the body to move the rotatable member relative to the body; and
    a second shaft being positioned between the rotatable member and the compression pad, wherein engagement between the first shaft and the second shaft causes a compounding of the amount of compression provided by the compression pad; and wherein the second shaft comprises a threaded member and the threaded member of the second shaft is threadably engaged by the first shaft.

17. The radial artery compression device of claim 16, wherein rotation of the rotatable member results in axial movement of the rotatable member towards or away from the body.

18. The radial artery compression device of claim 17, wherein the rotation of the rotatable member results in axial movement of the compression pad towards or away from the body.

19. The radial artery compression device of claim 18, wherein the compounding of the amount of compression results in a greater amount of axial movement of the compression pad relative to the body pursuant to a predetermined amount of rotation of the rotatable member than the amount of axial movement of the rotatable member relative to the body pursuant to the predetermined amount of rotation of the rotatable member.

20. The radial artery compression device of claim 16, wherein the first shaft threadably engages a threaded aperture positioned through the body.

21. The radial artery compression device of claim 16, further comprising a viewing window.

22. The radial artery compression device of claim 21, wherein the viewing window is positioned within a central void of the rotatable member.

* * * * *